(12) United States Patent
Fallin et al.

(10) Patent No.: US 6,645,227 B2
(45) Date of Patent: Nov. 11, 2003

(54) SUTURE ANCHOR

(75) Inventors: T. Wade Fallin, Hyde Park, UT (US); Daniel E. Gerbec, Logan, UT (US); Gordon Baker, Nibley, UT (US)

(73) Assignee: Stryker Endoscopy, San Jose, CA (US)

( * ) Notice: Subject to any disclaimer, the term of this patent is extended or adjusted under 35 U.S.C. 154(b) by 0 days.

(21) Appl. No.: 09/990,033

(22) Filed: Nov. 21, 2001

(65) Prior Publication Data

US 2003/0097150 A1 May 22, 2003

(51) Int. Cl.[7] ............................................... A61B 17/04
(52) U.S. Cl. ........................................ 606/232; 606/72
(58) Field of Search .............................. 604/177, 192; 606/72, 74, 232, 104, 73; 411/2–4, 340

(56) References Cited

U.S. PATENT DOCUMENTS

| | | |
|---|---|---|
| 3,716,058 A | 2/1973 | Tanner |
| 4,669,473 A | 6/1987 | Richards et al. |
| 4,741,330 A | 5/1988 | Hayhurst |
| 4,898,156 A | 2/1990 | Gatturna et al. |
| 4,899,743 A | 2/1990 | Nicholson et al. |
| 4,946,468 A | 8/1990 | Li |
| 5,002,550 A | 3/1991 | Li |
| 5,041,129 A | 8/1991 | Hayhurst et al. |
| 5,046,513 A | 9/1991 | Gatturna et al. |
| 5,192,303 A | 3/1993 | Gatturna et al. |
| 5,203,787 A | 4/1993 | Noblitt et al. |
| 5,207,679 A | 5/1993 | Li |
| 5,358,511 A | 10/1994 | Gatturna et al. |
| 5,403,348 A | 4/1995 | Bonutti |
| 5,464,425 A | 11/1995 | Skiba |
| 5,527,343 A | 6/1996 | Bonutti |
| 5,540,718 A | 7/1996 | Bartlett |
| 5,549,630 A | 8/1996 | Bonutti |
| 5,554,171 A | 9/1996 | Gatturna et al. |
| 5,584,862 A | 12/1996 | Bonutti |
| 5,626,612 A | 5/1997 | Bartlett |
| 5,683,418 A | 11/1997 | Luscombe et al. |
| 5,718,717 A | 2/1998 | Bonutti |
| 5,733,306 A | 3/1998 | Bonutti |
| 5,782,862 A | 7/1998 | Bonutti |
| 5,782,863 A | 7/1998 | Bartlett |
| 5,845,645 A | 12/1998 | Bonutti |
| 5,871,503 A | 2/1999 | Bartlett |
| 5,879,372 A | 3/1999 | Bartlett |
| 5,885,294 A * | 3/1999 | Pedlick et al. ................. 606/80 |
| 5,897,574 A | 4/1999 | Bonutti |
| 5,941,900 A | 8/1999 | Bonutti |
| 5,948,002 A | 9/1999 | Bonutti |
| 5,961,538 A | 10/1999 | Pedlick et al. |
| 5,980,558 A * | 11/1999 | Wiley .......................... 606/232 |
| 5,980,559 A | 11/1999 | Bonutti |
| 6,033,430 A | 3/2000 | Bonutti |
| 6,077,292 A | 6/2000 | Bonutti |
| 6,146,407 A | 11/2000 | Krebs |
| 6,146,408 A | 11/2000 | Bartlett |
| 6,165,203 A | 12/2000 | Krebs |
| 6,270,518 B1 | 8/2001 | Pedlick et al. |

\* cited by examiner

Primary Examiner—Julian W. Woo
(74) Attorney, Agent, or Firm—Workman Nydegger

(57) ABSTRACT

A suture anchor includes a placement portion frangably connected to an attachment portion. The attachment portion includes an outwardly projecting barb. During insertion of the suture anchor within a bore hole formed on a bone, the barb scores at least a portion of the bone bounding the bore hole. Once the suture anchor is disposed within the bore hole, a withdrawal force is applied to the suture anchor such that the attachment portion thereof rotates within the bore hole and disconnects from the placement portion. In an alternative embodiment, the suture anchor can be formed without the outwardly projecting barb.

49 Claims, 29 Drawing Sheets

SUTURE ANCHOR

CROSS-REFERENCE TO RELATED APPLICATIONS

Not applicable.

BACKGROUND OF THE INVENTION

1. The Field of the Invention

The present invention relates to implantable suture anchors used for surgically attaching soft tissue to bone, as well as instrumentation and methods for deploying such anchors.

2. The Relevant Technology

One common type of orthopedic, i.e., bone related, injury is the tearing of soft tissue, such as tendons, ligaments, and muscles. Such injuries often result in at least a portion of the soft tissue being separated from the bone so that the soft tissue no longer functions in its intended manner. A common surgical procedure to remedy this injury is to mechanically secure the torn portion of the soft tissue back to the bone. Such mechanical attachment can be temporary in that the soft tissue eventually reattaches itself to the bone if held in contact therewith for a sufficient period of time.

A suture anchor is one type of mechanical device that is used to secure soft tissue to bone. Although bone can have different consistencies at different locations, most bone comprises a hard outer surface, referred to as cortical bone. The cortical bone bounds a softer, spongy type bone referred to as cancellous bone. Most suture anchors comprise a small metal or plastic fixture which has a suture line secured thereto.

Attachment of the suture anchor to the bone generally entails forming a hole through the cortical bone and into the cancellous bone. The suture anchor is then inserted into the portion of the hole bounded by the softer cancellous bone. Once inserted, the suture anchor is manipulated so as to be securely wedged within the hole. The surgeon then uses the suture, which is attached to the suture anchor and extends out of the hole, to securely tie the soft tissue to the bone.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF EMBODIMENTS

Figure 1:
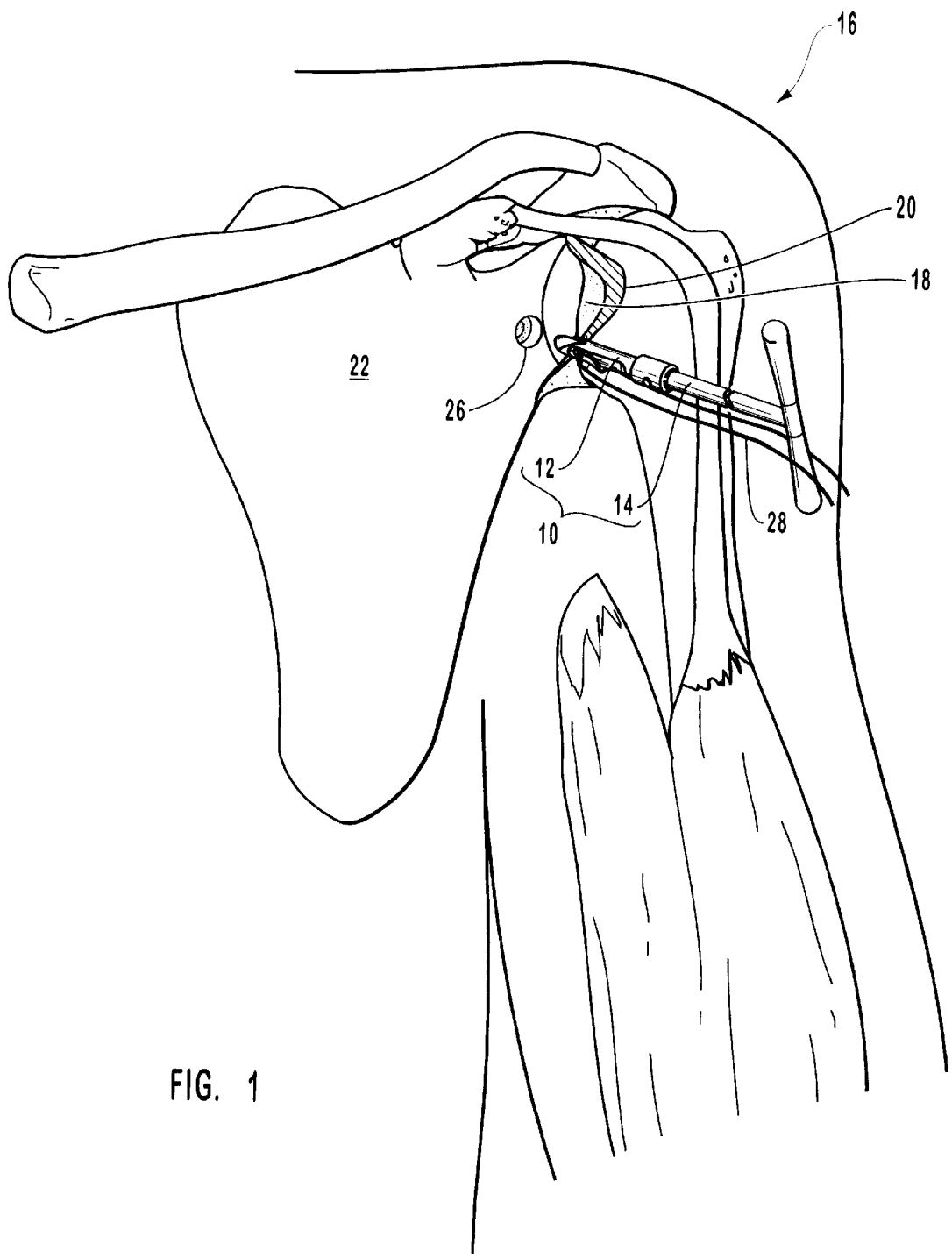
FIG. 1 is a perspective view of one embodiment of a suture anchor assembly being used to secure soft tissue torn away at a shoulder.

Depicted in FIG. 1 is one embodiment of a suture anchor assembly 10 incorporating features of the present invention. In general, suture anchor assembly 10 comprises a suture anchor 12 having an inserter 14 attached thereto. Sutures anchor 12 is configured for attachment to bone so as to subsequently facilitate attaching soft tissue, such as tendons, ligaments, muscles, or the like, either directly or indirectly to the bone.

By way of example, and not by limitation, depicted in FIG. 1 is a shoulder 16. A ligament 18 has a free end 20 which is shown as being torn away from a glenoid rim of scapula bone 22. As will be discussed below in greater detail, a bore hole 26 is formed on the glenoid rim of scapula bone 22 at the location for the attachment of ligament 18. At least a portion of suture anchor 12, having a suture line 28 passing therethrough, is inserted and secured within bore hole 26. Once secured therein, suture line 28 is used to secure free end 20 of ligament 18 to scapula bone 22. It is appreciated that suture anchor 12 in FIG. 1 is not necessarily to scale in that suture anchor 12 would likely be smaller relative to shoulder 16.

Figure 2:
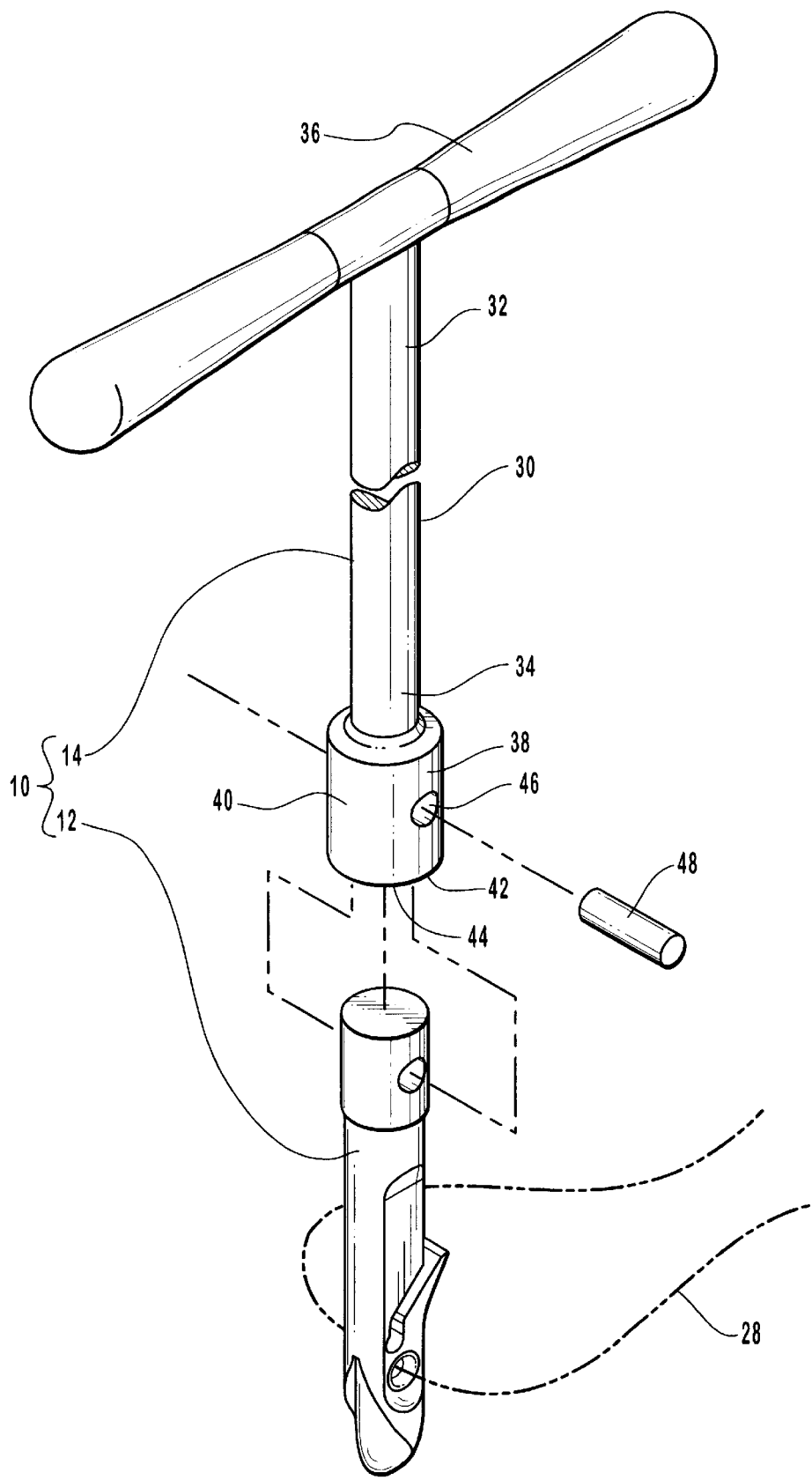
FIG. 2 is a perspective view of the suture anchor assembly shown in FIG. 1 in a disassemble state.
Figure 3:
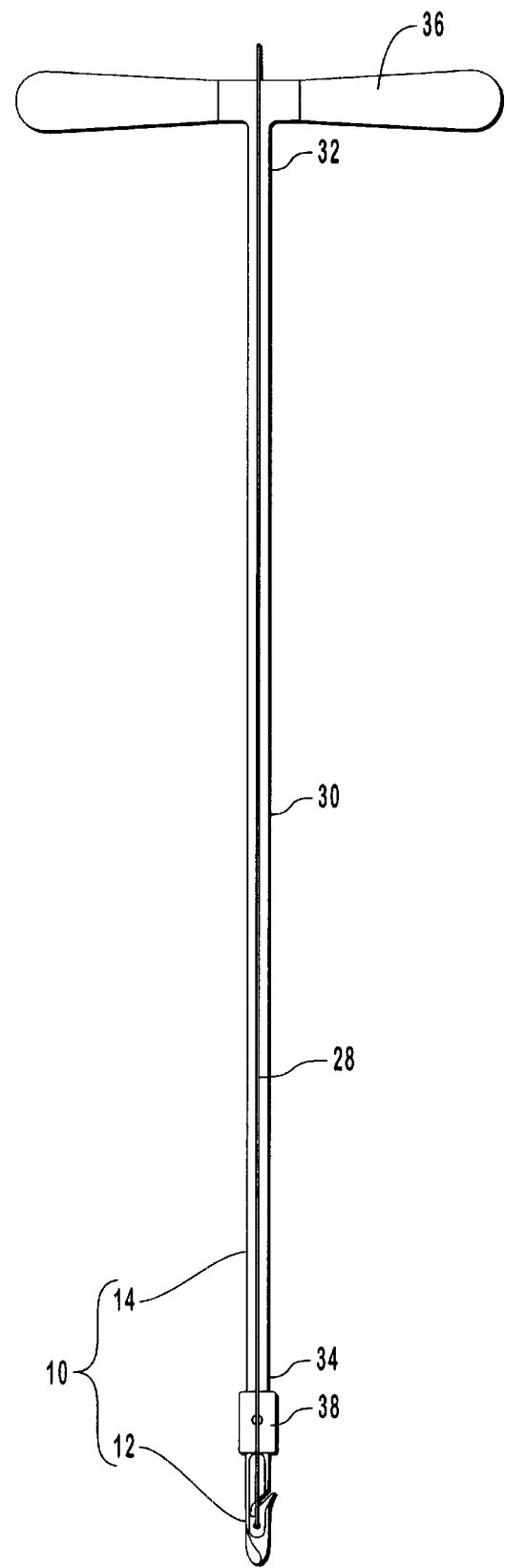
FIG. 3 is a elevated side view of the suture anchor assembly shown in FIG. 1 in an assembled state.

As depicted in FIGS. 2 and 3, inserter 14 comprises an elongated shaft 30 that extends from a proximal end 32 to an opposing distal end 34. An elongated handle 36 orthogonally outwardly projects from proximal end 32 of shaft 30. Handle 36 is used by the surgeon to hold and manipulate inserter 14 and can come in a variety of different configurations. For example, handle 36 can comprise an enlarged circular disk or have any other desired configuration. In other embodiments, inserter 14 can also be formed without handle 36.

Formed at distal end 34 of shaft 30 is an enlarged head 38. Head 38 has a side wall 40 that extends to an end face 42. Recessed within end face 42 is a substantially cylindrical socket 44 (see FIG. 7). A bore 46 extends through side wall 40 to socket 44 and, as discussed below in greater detail, is configured to receive a pin 48. In alternative embodiments, it is appreciated that head 38 and shaft 30 can have the same outside diameter. Furthermore, the exterior surface of head 38 and shaft 30 need not be round but can have any desired configuration.

Figure 4:
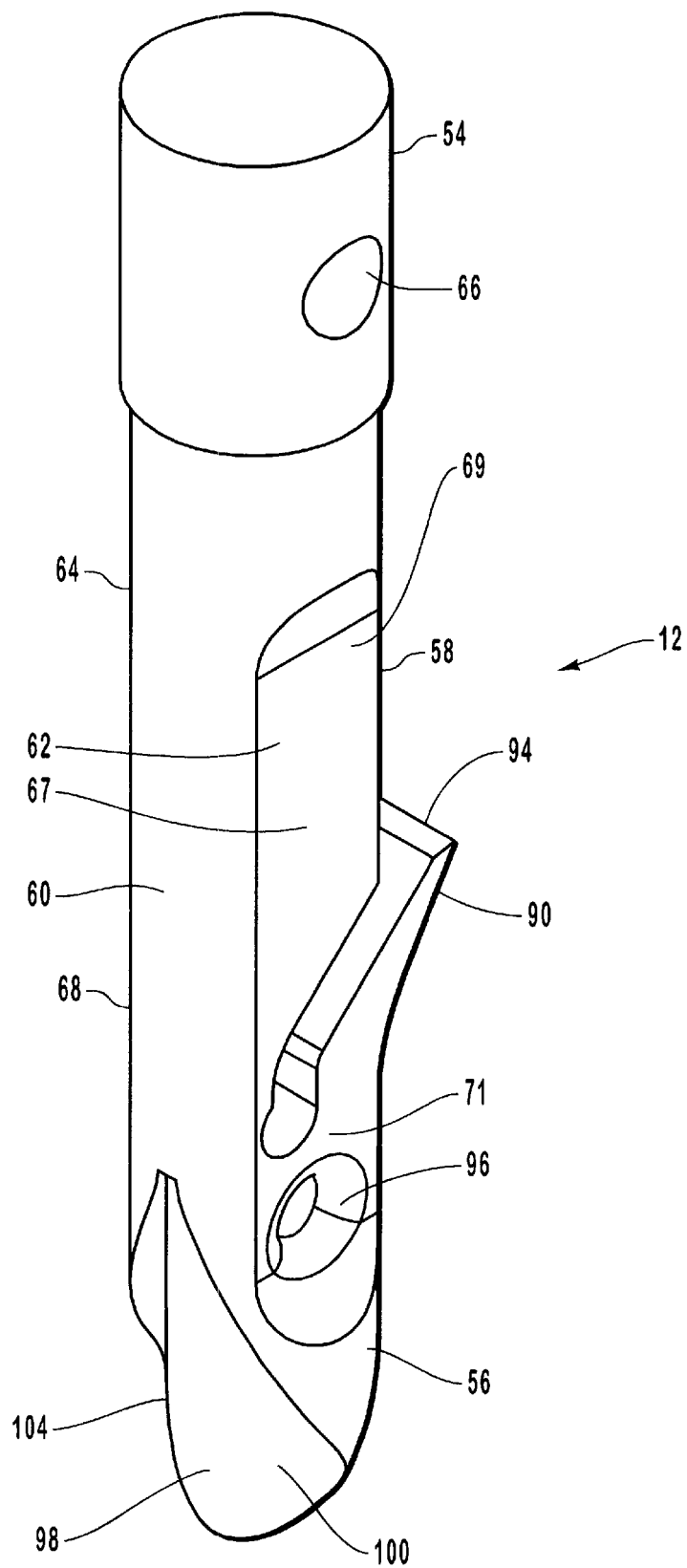
FIG. 4 is a perspective view of the suture anchor of the suture anchor assembly shown in FIG. 2.
Figure 5:
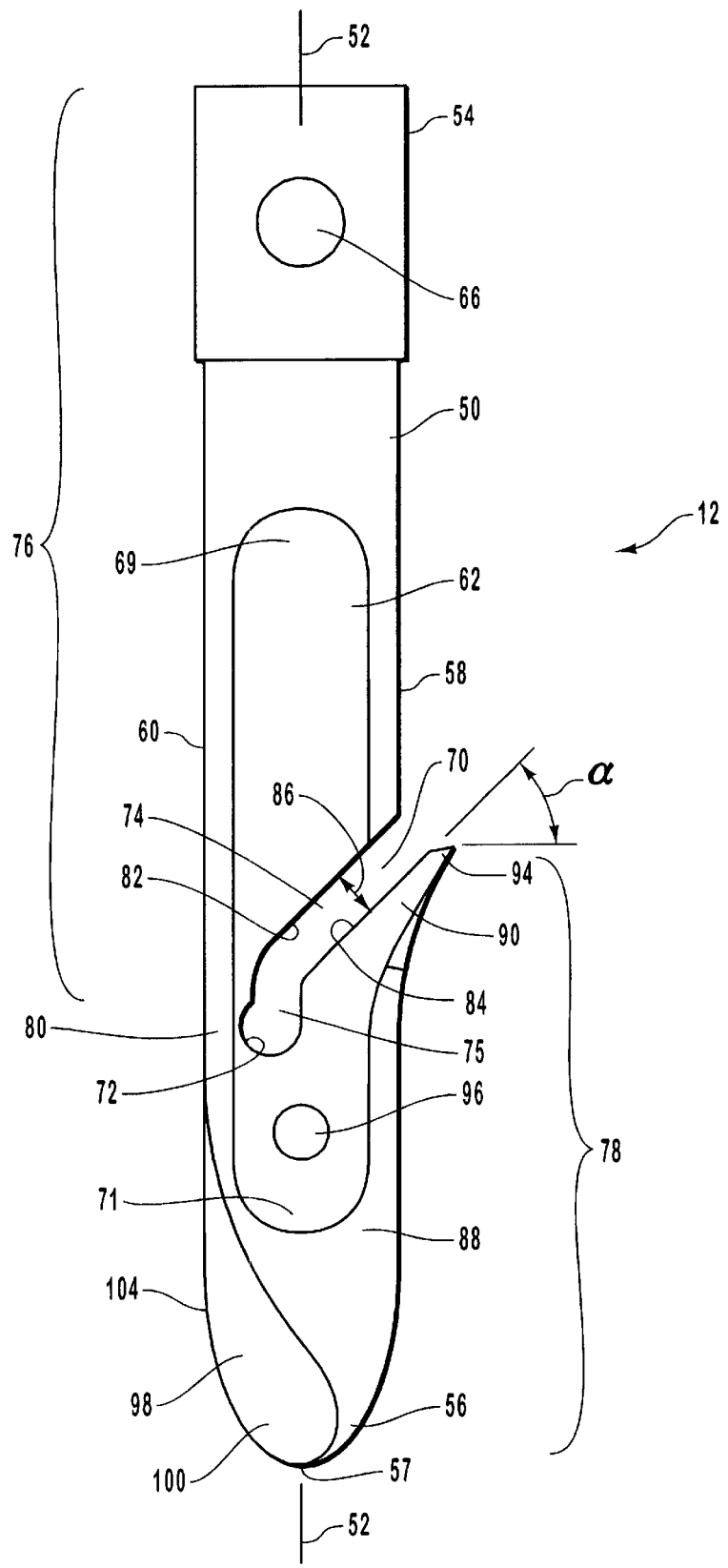
FIG. 5 is an elevated left side view of the suture anchor shown in FIG. 4.
Figure 6:
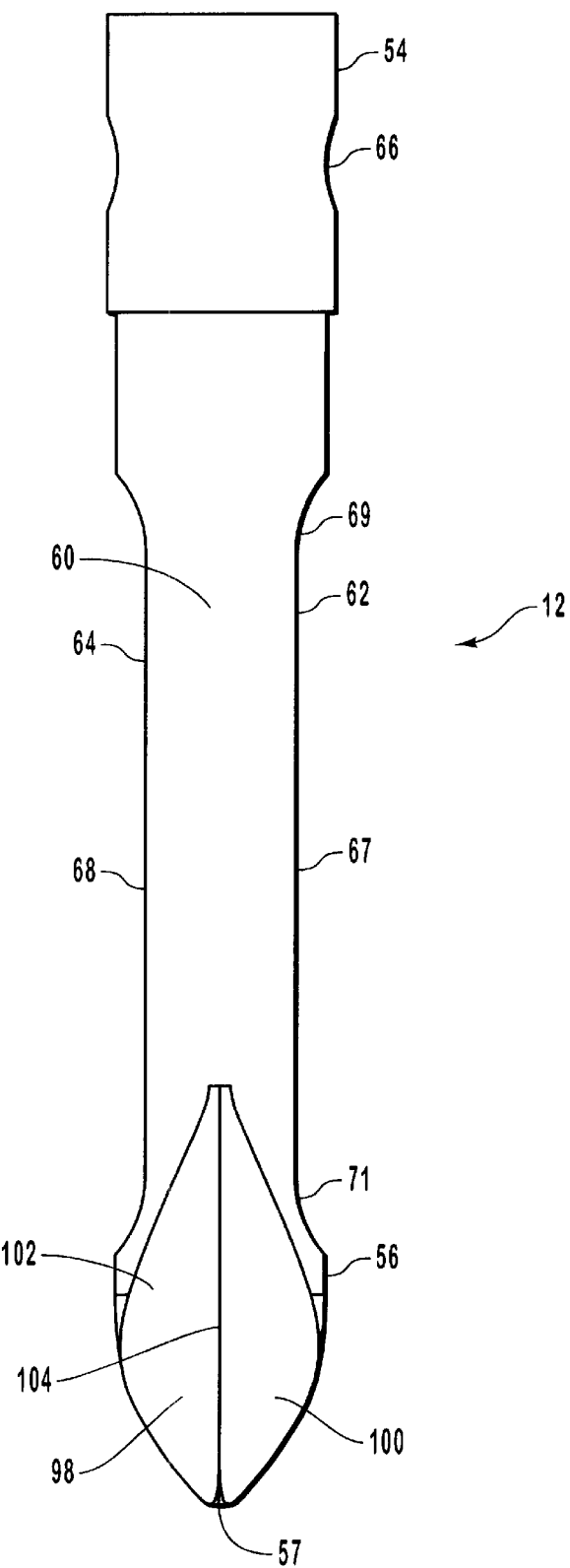
FIG. 6 is an elevated back side view of the suture anchor shown in FIG. 4.

As depicted in FIGS. 4–6, suture anchor 12 comprises an elongated body 50 having a central longitudinal axis 52 extending therethrough. Body 50 has a proximal end 54 and an opposing distal end 56. Distal end 56 terminates at a tip 57. Extending between ends 54 and 56, body 50 has a front face 58, an opposing back face 60, and opposing side faces 62 and 64. Body 50 has a substantially circular transverse cross sectional area with a flattened side wall 67 being formed along a longitudinal portion of side face 62 and a flattened side wall 68 being formed along a longitudinal portion of side face 64. Flattened side walls 67 and 68 are disposed in parallel alignment and each extend between a proximal end 69 and an opposing distal end 71. For a given transverse cross section of body 50, the diameter between side walls 67 and 68 is smaller than the diameter between front face 58 and back face 60.

Figure 7:
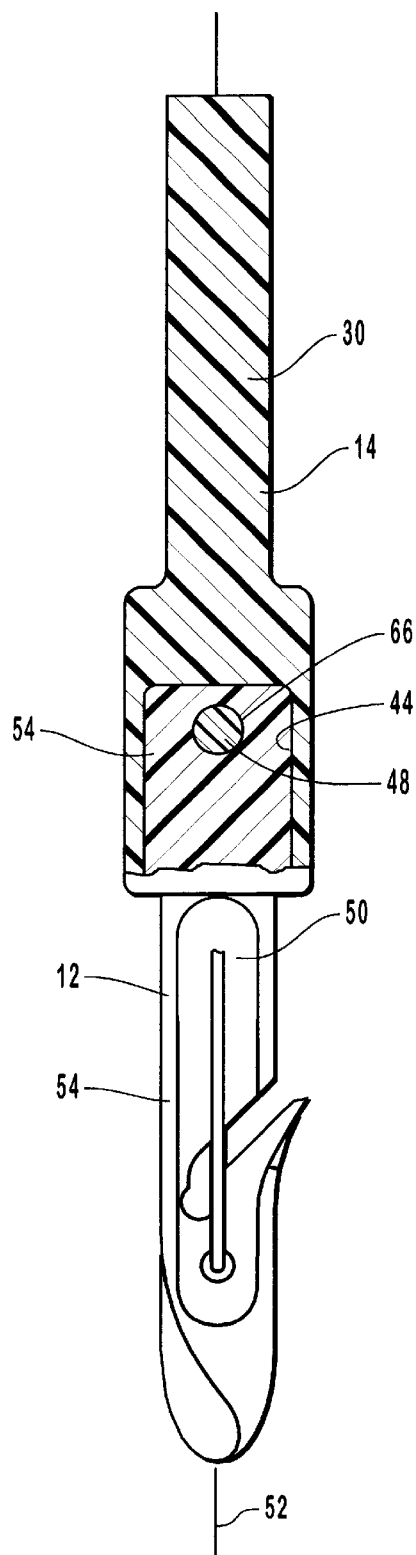
FIG. 7 is partially cut away elevated left side view of the suture anchor assembly shown in FIG. 3.

Transversely extending into and/or through proximal end 54 of body 50 is an annular bore 66. As depicted in FIG. 7, proximal end 54 of body 50 is configured to be received within socket 44 of inserter 14 such that bores 46 and 66 are aligned. In this configuration, pin 48 is press fit within the aligned bores 46 and 66 so as to securely connect inserter 14 and suture anchor 12 together. In this configuration, central longitudinal axis 52 of suture anchor 12 also centrally extends through shaft 30 of inserter 14.

In alternative embodiments, it is appreciated that socket 44 and proximal end 54 of suture anchor 12 can have any desired complementary configurations, such as polygonal or irregular configurations, that enable mating of the parts together. It is also appreciated that the configurations can be reversed such that socket 44 is formed on suture anchor 12.

Furthermore, bores 46 and 66 can have any desired configuration with pin 48 being configured to be received within aligned bores 46 and 66. Bores 46 and/or 66 can also be threaded to engage with a threaded pin 48. In yet other embodiments, it is appreciated that inserter 14 and suture anchor 12 can be rigidly secured together using any of a number of conventional connection methods. For example, the members can be directly crimped, welded, screwed, press fit, clamped, or otherwise secured together such as by the use of an adhesive with or without the use of socket 44.

Returning to FIG. 5, a slot 70 is formed starting at front face 58 and extending towards back face 60 so as to partially bisect elongated body 50 into two portions. Specifically, body 50 includes a placement portion 76 that extends between proximal end 54 and slot 70 and an attachment portion 78 that extends between slot 70 and distal end 56 of body 50. Attachment portion 78 has an aspect ratio of length-to-width that is greater than one. Slot 70 is bounded between a distal end face 82 of placement portion 76 (also referred to as an upper side wall) and a proximal end face 84 of attachment portion 78 (also referred to as a lower side wall). Each of end faces 82 and 84, and thus also slot 70, transversely extend between opposing side walls 67 and 68.

Slot 70 includes a linear portion 74 that terminates at a downwardly projecting lobe 75. Lobe 75 has an end face 72 which, in the embodiment depicted, is curved. A frangible strut 80 connects placement portion 76 and attachment portion 78 together. Frangible strut 80 extends between end face 72 and back face 60.

As discussed below in greater detail, when axis 52 is vertically disposed, proximal end face 84 is substantially disposed in a plane that is typically oriented at an angle α relative to the horizontal in a range between about 20° to about 70° and more commonly between about 30° to about 60°. In alternative embodiments, some of which will be discussed below, proximal end face 84 can be horizontally disposed or positioned at a variety of other angles. Proximal end face 84 can also be curved along a constant or irregular radius. In the embodiment depicted, distal end face 82 is disposed in a plane substantially parallel to proximal end face 84. Distal end face 82 can also be curved along a constant or irregular radius and can be disposed so that a gap 86 formed between end faces 82 and 84 varies or is substantially constant along the length of slot 70.

The size of gap 86 is largely a factor of the process used to form slot 70. For example, in one embodiment, end faces 82 and 84 can be biased together so that slot 70 merely comprises a crack formed therebetween. It is noted, however, that as gap 86 of slot 70 decreases or narrows at end face 72, the localized stress at end face 72 increases. Accordingly, by modifying end face 72 from a relatively large curved face to a narrowing crack, less force is required to propagate slot 70 across frangible strut 80, as will be discussed below. As such, end face 72, partially bounding frangible strut 80, is selectively configured based in part on the desired amount of force needed to produce failure of frangible strut 80. In one embodiment gap 86 may thus be relatively narrow at the mouth thereof adjacent to front face 58 but then widen at end face 72. The amount of force needed to produce failure of frangible strut 80 can also be adjusted by other variables such as the size of frangible strut 80 and the material thereof.

Figure 8:
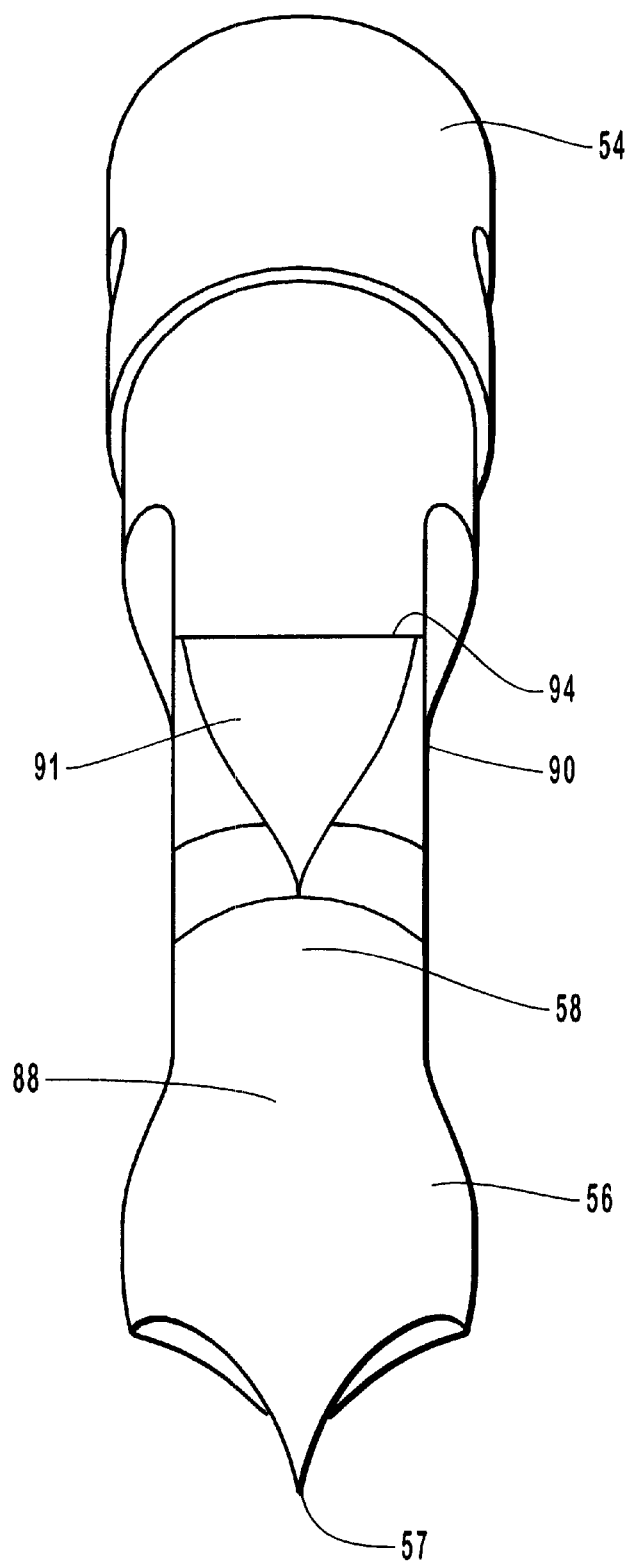
FIG. 8 is a back perspective view of the suture anchor shown in FIG. 4.

As depicted in FIGS. 5 and 8, attachment portion 78 comprises an attachment body 88 having a barb 90 outwardly projecting therefrom. Barb 90 has a substantially flat front face 91 that terminates at an elongated sharpened edge 94. In the embodiment depicted, barb 90 outwardly projects from proximal end face 84 at front face 58. In alternative embodiments, it is appreciated that barb 90 can extend from front face 58 at a variety of different locations between slot 70 and distal end 56. Furthermore, one or more barbs 90 can project from side face 62, side face 64, and/or front face 58 of attachment portion 78.

In one embodiment of the present invention, means are provided for coupling suture line 28 to attachment portion 78. By way of example and not by limitation, extending between flattened side walls 67, 68 on attachment portion 78 is a suture port 96. Suture port 96 allows suture line 28, which can comprise any form of line, to pass through attachment portion 78 (as shown in FIG. 2), thereby coupling therewith. In alternative embodiments, the means for coupling suture line 28 can comprise a slot that extends from front face 58, back face 60, or tip 57 of attachment portion 78 into attachment body 88, the slot being configured to receive suture line 28 therein.

In yet other embodiments of the means for coupling, suture port 96 need not extend between side walls 67, 68 but can form a passage that extends into and out of a portion of side wall 67 or side wall 68, the passage being configured to pass suture line 28 therethrough. It is appreciated that passages or holes can also be formed through a number of other locations on attachment portion 78, including barb 90, through which suture line 28 can be passed. In addition, suture line 28 can be coupled to attachment portion 78 such as by molding a portion of suture line 28 into attachment portion 78 or by securing suture line 28 to attachment portion 78 by welding, crimping, adhesive, or the like.

Although not required, as depicted in FIGS. 4–6, a plow 98 is formed on attachment portion 78. Plow 98 comprises a pair of opposing taped faces 100 and 102 that each extended to a sharpened edge 104. Sharpened edge 104 extends from tip 52 either to or adjacent to frangible strut 80 along back side 60. In alternative embodiments, sharpened edge 104 can extend over more or less of attachment portion 98.

Figure 9:
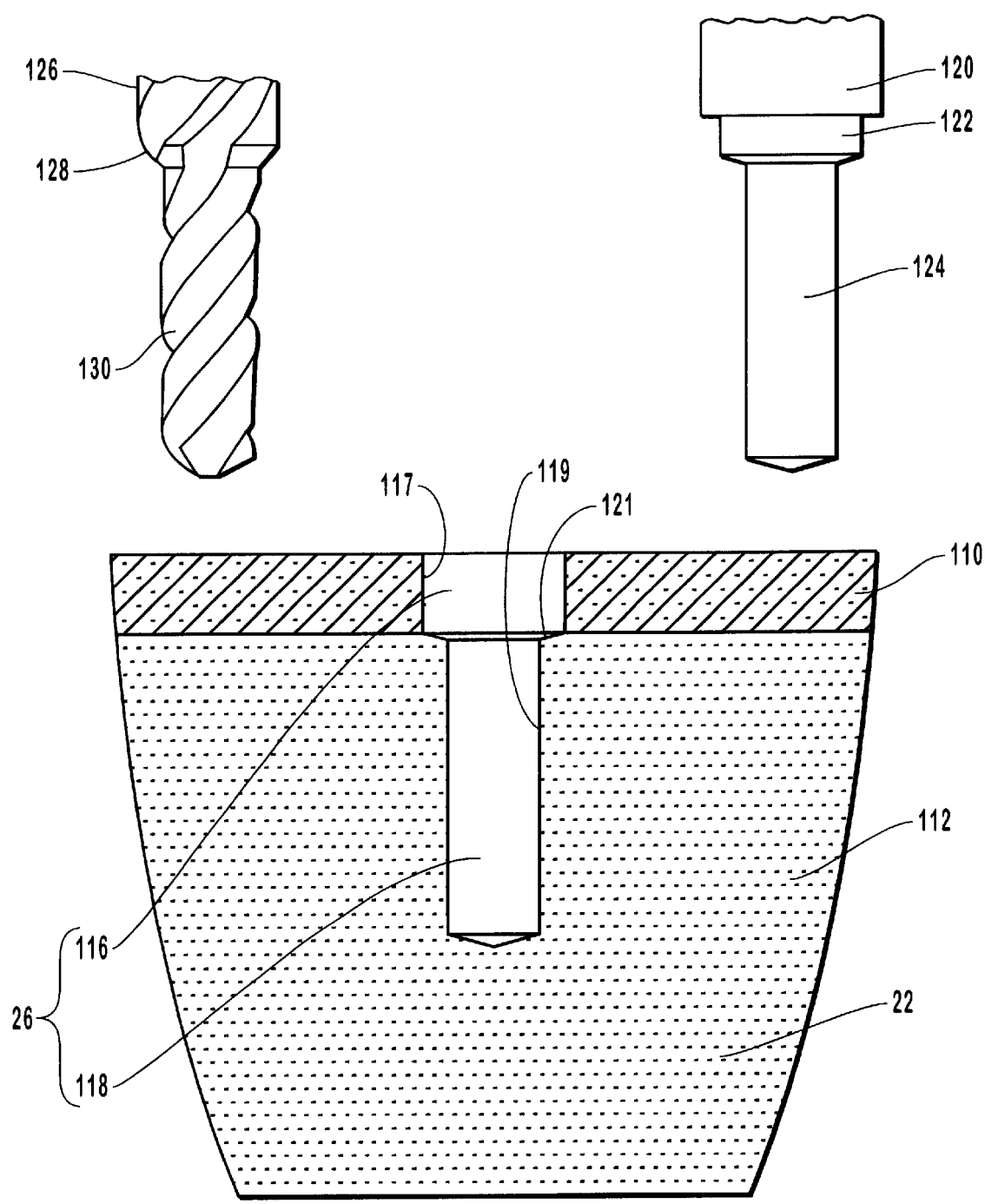
FIG. 9 is a cross sectional side view of bone shown in FIG. 1 having a bore hole formed therein by either a punch or a drill bit.

Depicted in FIG. 9, bone 22 is shown as having a hard cortical bone layer 110 over a softer cancellous bone layer 112. To facilitate attachment of suture anchor 12, bore hole 26 is formed extending into bone 22. Bore hole 26 comprises a first hole 116 extending through or at least partially through cortical bone layer 110 and a second hole 118 concentrically disposed within the first hole 116 and extending into cancellous bone layer 112. First hole 116 is bounded by an interior surface 117 while second hole 118 is bounded by an interior surface 119. Second hole 118 has a smaller maximum diameter than first hole 116 so that a shoulder 121 is formed therebetween.

In one embodiment, bore hole 26 can be formed by driving a punch 120 into bone 22. Punch 120 is shown having concentrically disposed bits 122 and 124 that are configured complementary to bore hole 26. Alternatively, separate punches can be used to separately form first hole 116 and second hole 118. In contrast to using punch 120, a drill bit 126 can be used to form bore hole 26. Drill bit 126 is also shown as having concentrically disposed drilling bits 128 and 130 that are configured complementary to bore hole 26. Separate drill bits can also be used to separately form first hole 116 and second hole 118. Other methods known in the art can also be used to form bore hole 26. Furthermore, as will be disclosed below, suture anchor 12 can also be placed without the formation of bore hole 26.

Figure 10:
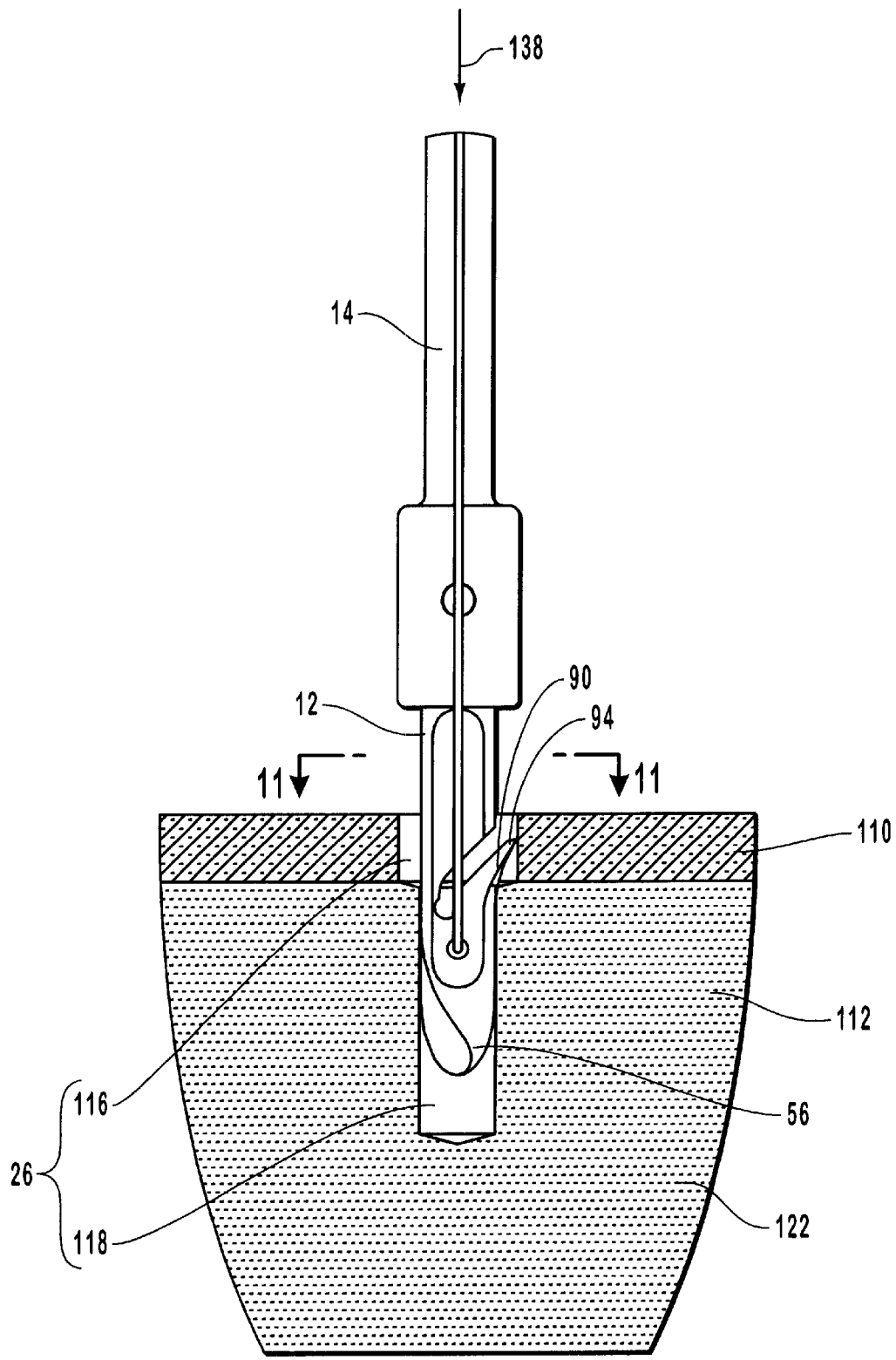
FIG. 10 is an elevated side view of the suture anchor shown in FIG. 4 being inserted into the bore hole of FIG. 9.
Figure 11:
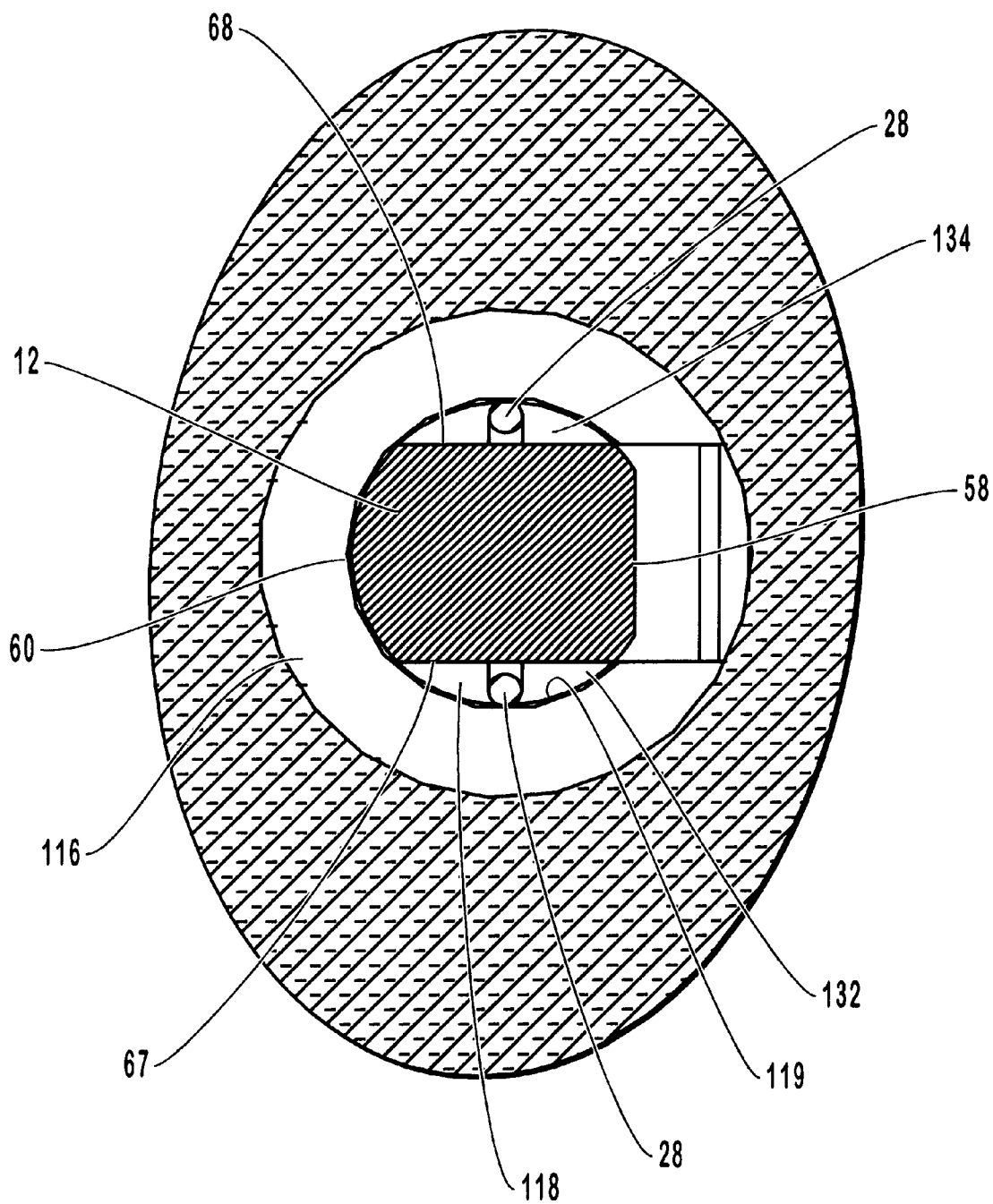
FIG. 11 is a cross sectional top plan view taken along section lines 11—11 of FIG. 10.

As depicted in FIGS. 10 and 11, by applying an insertion force on inserter 14 in the direction of arrow 138, distal end 56 of suture anchor 12 is initially advanced into second hole 118 so that barb 90 is received within first hole 116. In one embodiment, the insertion force is applied along the central longitudinal axis of suture anchor 12. First hole 116 has a diameter equal to or larger than the maximum transverse diameter of suture anchor 12 at edge 94 of barb 90 so that barb 90 can be inserted into first hole 116 without having to score cortical bone layer 110. As used in the specification and appended claims, the term "score" used in associate with bone means that that portion of the bone is displaced such as by being compressed, sliced, cut, or combinations thereof and the like. In contrast to first hole 116, second hole 118 has a diameter smaller than the maximum transverse diameter of suture anchor 12 at edge 94 of barb 90.

It is further noted with regard to FIG. 11 that because the diameter between flattened side walls 67 and 68 is smaller than the diameter between front face 58 and back face 60, a gap 132 is formed between side wall 67 of suture anchor 12 and interior surface 119 of second hole 118. A similar gap 134 is also formed between side wall 68 of suture anchor 12 and interior surface 119 of second hole 118. Gaps 132 and 134 provide an open space for suture line 28 so that suture line 28 is not damaged as suture anchor 12 is placed and secured within bore hole 26.

Figure 12A:
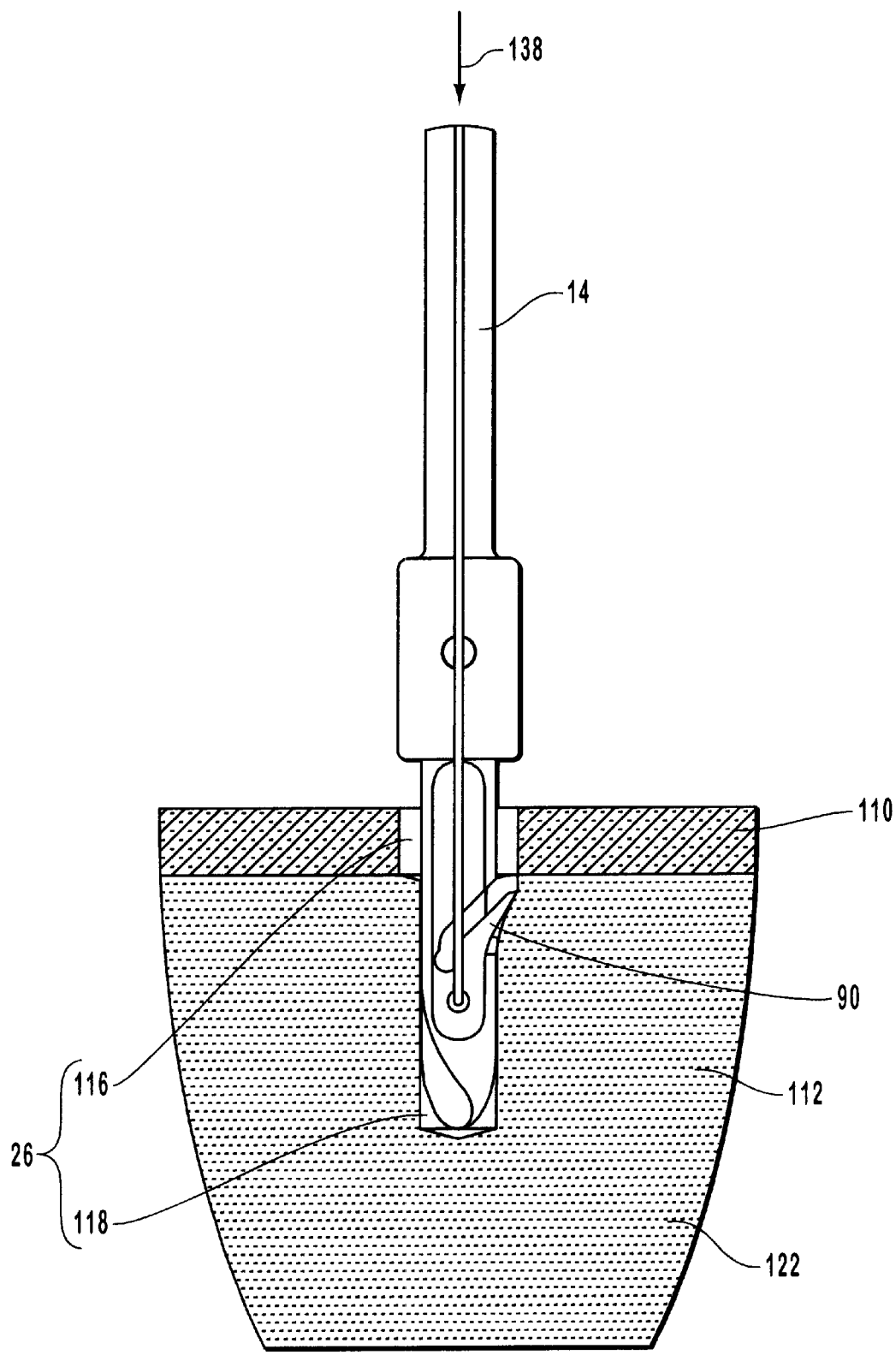
FIG. 12A is an elevated side view of the suture anchor shown in FIG. 10 being fully inserted within the bore hole.

Next, as depicted in FIG. 12A, additional force is applied to inserter 14 driving all of attachment portion 78 of suture anchor 12 into second hole 118 and thus into cancellous bone layer 112. In so doing, barb 90 scores a portion of cancellous bone 112. In one embodiment, barb 90 scores bone layer 112 to a depth of at least 0.3 mm and more typically to at least 0.5 mm from interior surface 119. This depth can be increased or decreased depending on the intended use of suture anchor 12. In the act depicted in FIG. 12A, second hole 118 is formed to a predefined depth such that the surgeon knows that suture anchor 12 is inserted to a proper depth when suture anchor 12 hits the bottom of second hole 118.

Figure 12B:
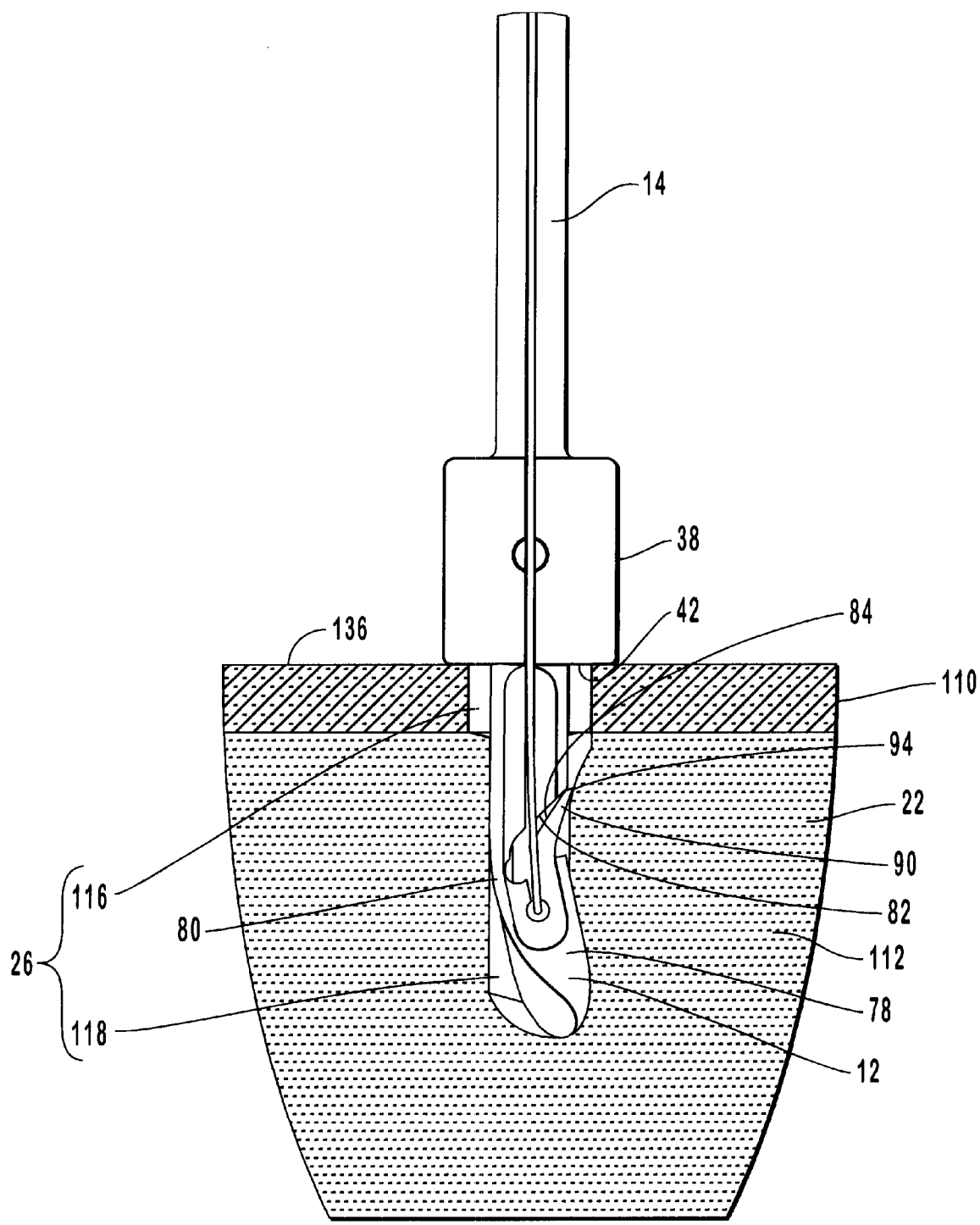
FIG. 12B is an elevated side view of an alternative embodiment of a suture anchor being fully inserted within the bore hole of FIG. 9.

Depending on the person and the location at which bore hole 26 is formed, the bone material may be harder or softer. Furthermore, bone closer to joints can have a much thicker layer of the harder cortical bone. Accordingly, as depicted in FIG. 12B, where the bone material is harder and/or where suture anchor 12 is made of a softer or more flexible material, as the additional force is applied to inserter 14 driving attachment portion 78 of suture anchor 12 into second hole 118, the force of the bone against barb 90 causes attachment portion 78 to either flex under elastic deformation and/or bend under plastic deformation at frangible strut 80. As a result, a portion of barb 90 and/or proximal end face 84 is biased against distal end face 82. It is noted that in this bent or flexed position, edge 94 of barb 90 still outwardly projects so as to score cancellous bone layer 112.

The supporting of barb 90 and/or proximal end face 84 against distal end face 82 ensures that at least a portion of barb 90 scores bone material during insertion of attachment portion 78 into bone layer 112. Furthermore, the above supporting of barb 90 and/or proximal end face 84 prevents over flexing or bending of frangible strut 80 during the insertion of attachment portion 78 which could produce premature failure of frangible strut 80. As such, in one embodiment the gap between proximal end face 84 and distal end face 82 should be sufficiently small that barb 90 and/or proximal end face 84 biases against distal end face 82 prior to failure of frangible strut 80. During some uses, it is appreciated that attachment portion 78 may only slightly bend or flex so that barb 90 is moved toward upper side wall 82 but does not contact therewith.

As also depicted in FIG. 12B, to help inform the surgeon as to when suture anchor 12 is fully inserted into bore hole 26, head 38 of inserter 14 can be formed with a diameter that is larger than the diameter of first hole 116. As a result, end face 42 of head 38 biases against a top surface 136 of bone 22 when suture anchor 12 is fully inserted. As such, suture anchor 12 need not contact the bottom of bore hole 26.

Figure 13:
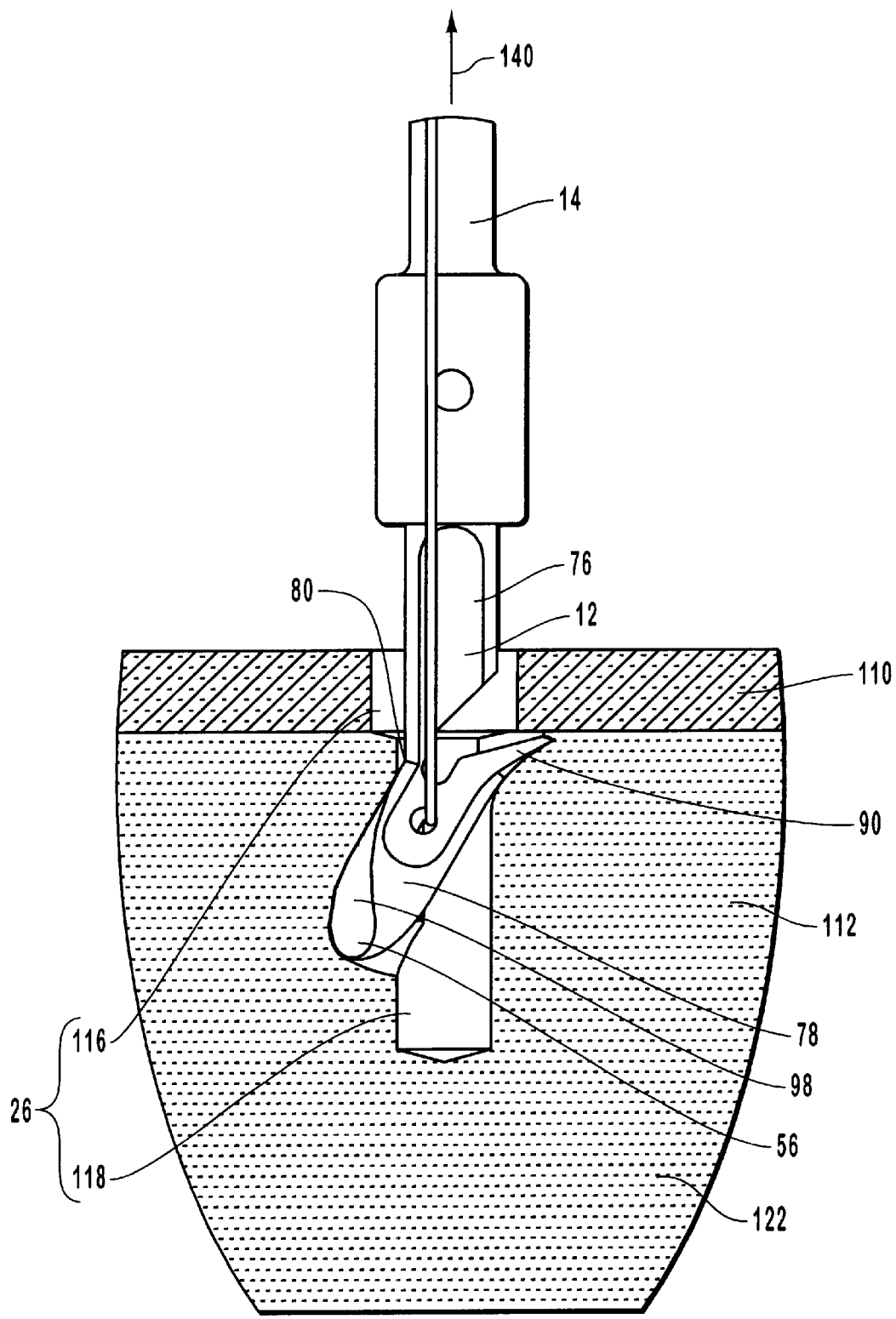
FIG. 13 is an elevated side view of an attachment portion of the suture anchor shown in FIG. 12A being rotated within the bore hole.

Next, as depicted in FIG. 13, once attachment portion 78 is inserted within second hole 118, a upward withdrawal force is applied to inserter 14 in the direction of arrow 140. As the withdrawal force is applied, barb 90 penetrates into the bone material. Barb 90 acts as a pivot point causing distal end 56 of attachment portion 78 to rotate clockwise (in the view shown in FIG. 13) so that plow 98 also penetrates into the bone material. Attachment portion 78 continues to rotate until frangible strut 80 is bent or otherwise deformed to such an extent that it fails, thereby separating placement portion 76 of suture anchor 12 from attachment portion 78.

As previously discussed, frangible strut 80 and/or the configuration of slot 70 adjacent thereto can be selectively modified so that frangible strut 80 fails upon the application of a predefined withdrawal force. This predefined withdrawal force that produces failure of frangible strut 80 can be different for different embodiment and for different uses. In one embodiment, this predefined withdrawal is in a range between about 2 lbs to about 30 lbs with about 5 lbs to about 10 lbs being more preferred. In other embodiments, the force can be greater or smaller.

Figure 14:
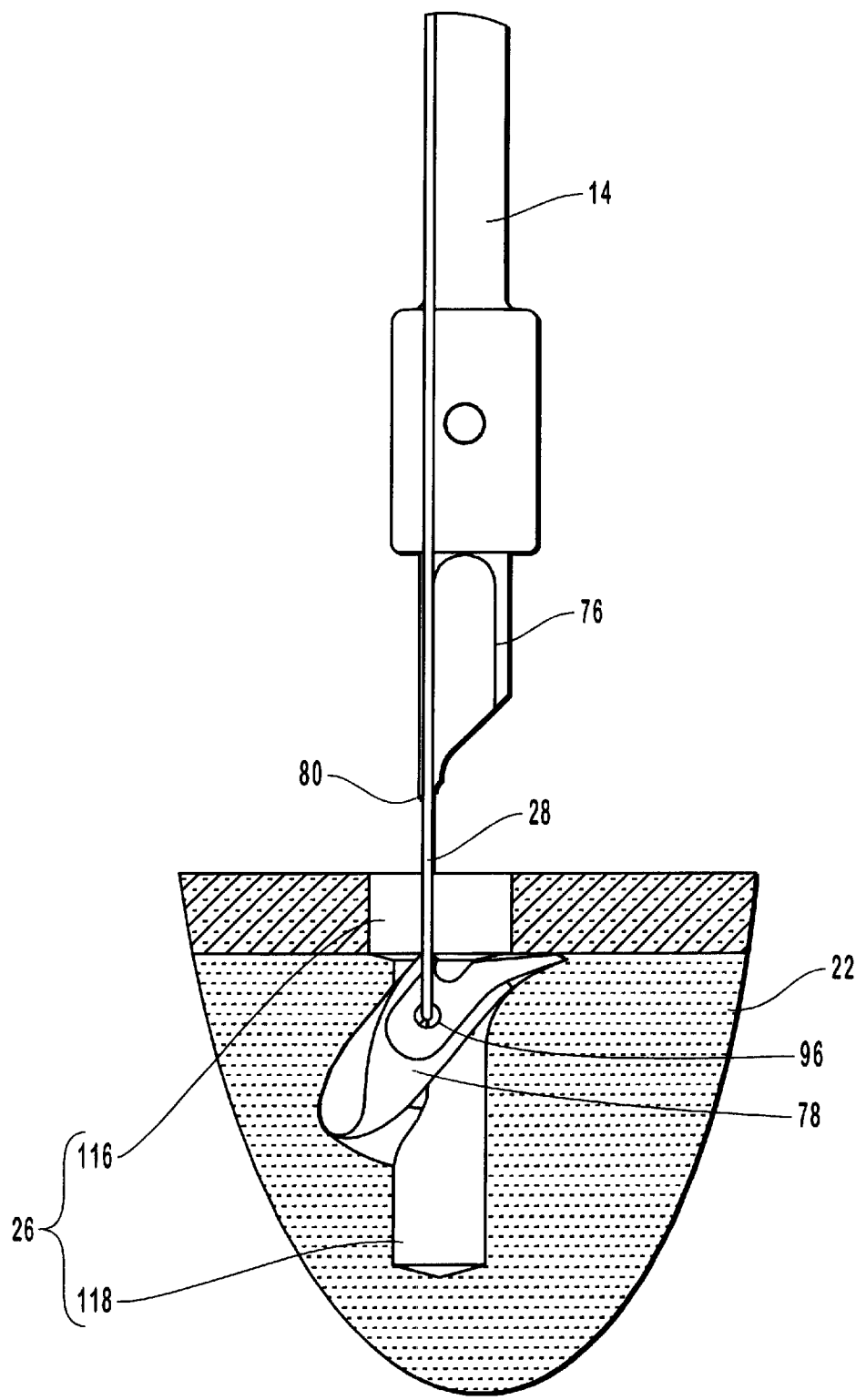
FIG. 14 is an elevated side view of the fully rotated attachment portion shown in FIG. 13 being separated from the placement portion.

As depicted in FIG. 14, once frangible strut 80 fails, placement portion 76 of suture anchor 12 is removed from bore hole 26 with inserter 14. As a result of the rotation of attachment portion 78 within the bone material, attachment portion remains secured within the bone material. In this position, suture line 28 passes through suture port 96 and extends out of bore hole 26.

Figure 15:
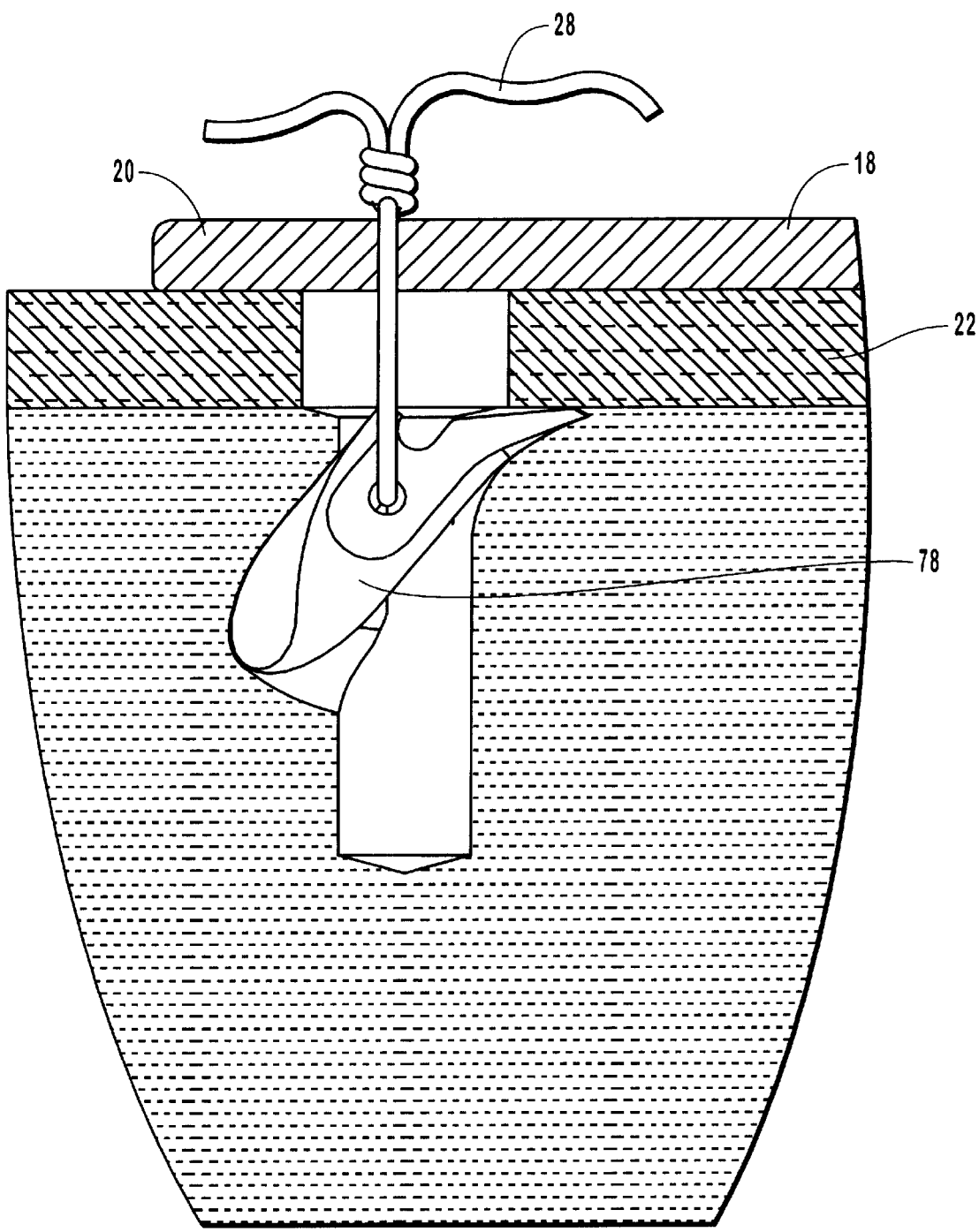
FIG. 15 is an elevated side view of the suture anchor shown in FIG. 14 being used to secure soft tissue to the bone by use of a suture.

Finally, as depicted in FIG. 15, suture line 28 is used in any of a number of conventional manners to secure free end 20 of ligament 18 to bone 22.

In one embodiment of the present invention, means are provided for connecting placement portion 76 to attachment portion 78 such that when an insertion force is applied to placement portion 76 and attachment portion 78 as they are being directed into the bore hole, barb 90 scores at least a portion of the bone bounding the bore hole while maintaining connection between placement portion 76 and attachment portion 78 and when a withdrawal force, substantially opposite of the insertion force, is applied to placement portion 76 and attachment portion 78, attachment portion 78 rotates within the bore hole causing placement portion 76 and attachment portion 78 to disconnect. By way of example and not by limitation one embodiment of such means for connecting comprises frangible strut 80 as discussed above. Alternative embodiments of the means for connecting include the alternative frangible strut placements, configurations, and connections as discussed herein. For example, such alternatives include the frangible struts as discussed below with regard to FIGS. 16–18 and 22.

Figure 16:
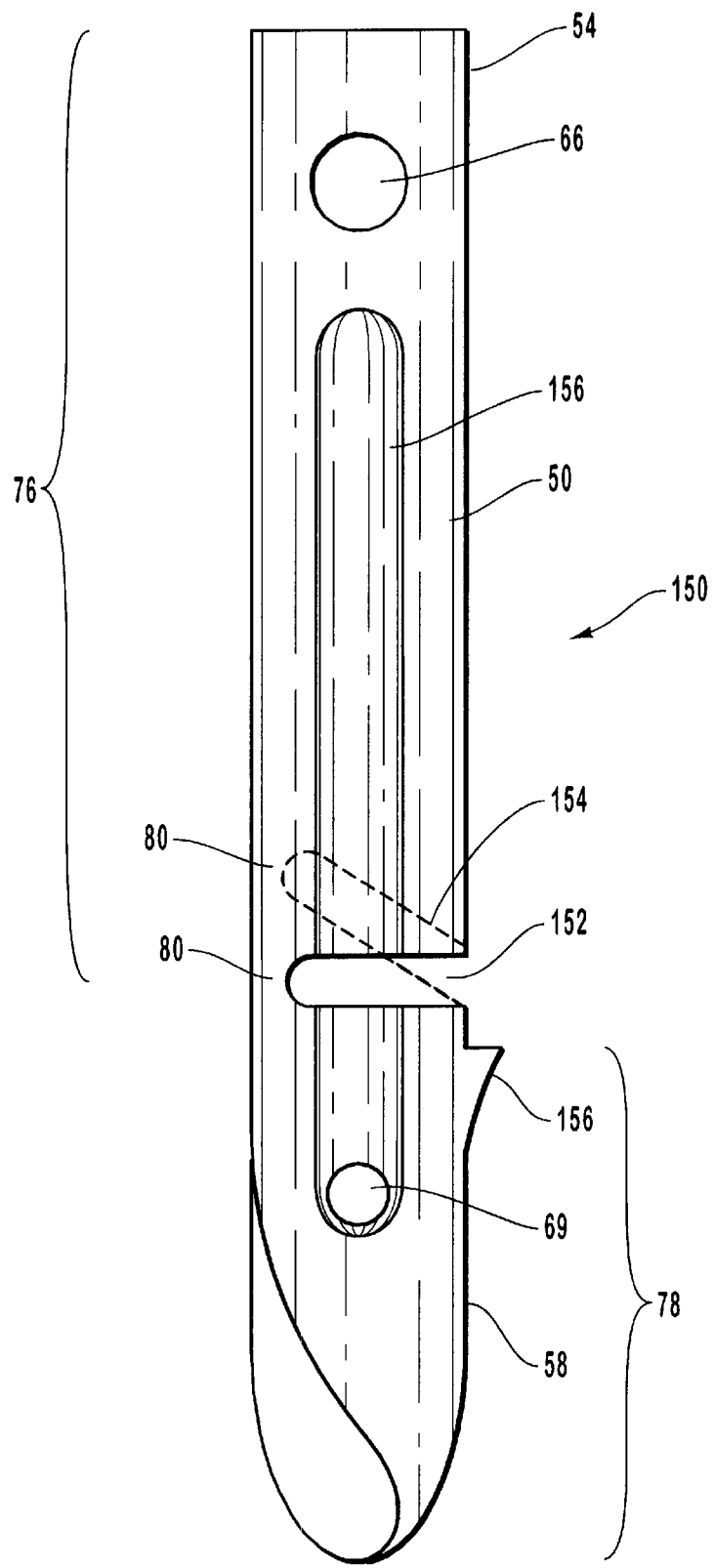
FIG. 16 is an elevated side view of an alternative embodiment of a suture anchor having slots extending from the front face thereof at various angles.

Depicted in FIG. 16 is an alternative embodiment of a suture anchor 150 that operates in substantially the same way suture anchor 12. Like elements between suture anchor 150 and suture anchor 12 are identified by like reference characters. In contrast to suture anchor 12, suture anchor 150 has a bisecting slot 152 that extends horizontally into body 50 instead of at a downward angle. Alternatively, as depicted by dashed lines 154, the slot can also upwardly extend into body 50.

Projecting from front face 58 of attachment portion 78 is a barb 156. In contrast to barb 90 of suture anchor 12, barb 156 is disposed below slot 152 so as not to be directly bounded thereby. Furthermore, in contrast to flattened sidewalls 67 and 68 of suture anchor 12, a grooved channel 156 extends along each side of suture anchor 150 so as to intersect with suture port 69. Grooved channels 156 are configured to receive suture line 28.

Figure 17:
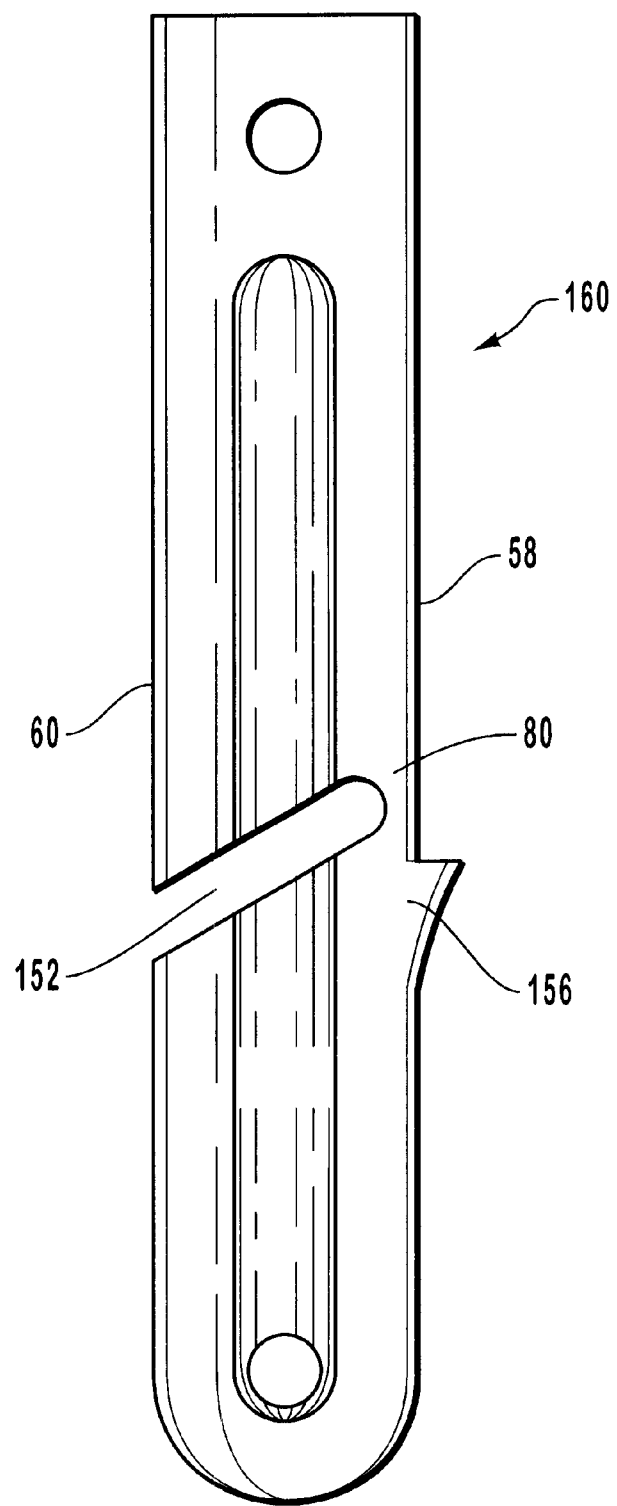
FIG. 17 is an elevated side view of an alternative embodiment of a suture anchor having a slot extending from the back face thereof.

Depicted in FIG. 17 is an alternative embodiment of a suture anchor 160. Suture anchor 160 is similar to suture anchor 150 except that slot 152 extends from back face 60 toward front face 58. Again, slot 152 can be oriented a virtually any angle In this embodiment, frangible strut 80 is formed along front face 58. Barb 156 projects from front face 58 below frangible strut 80. In yet another alternative embodiment, it is appreciated that separate slots can project from both front face 58 and back face 60 so that the frangible strut is formed between the opposing slots.

Figure 18:
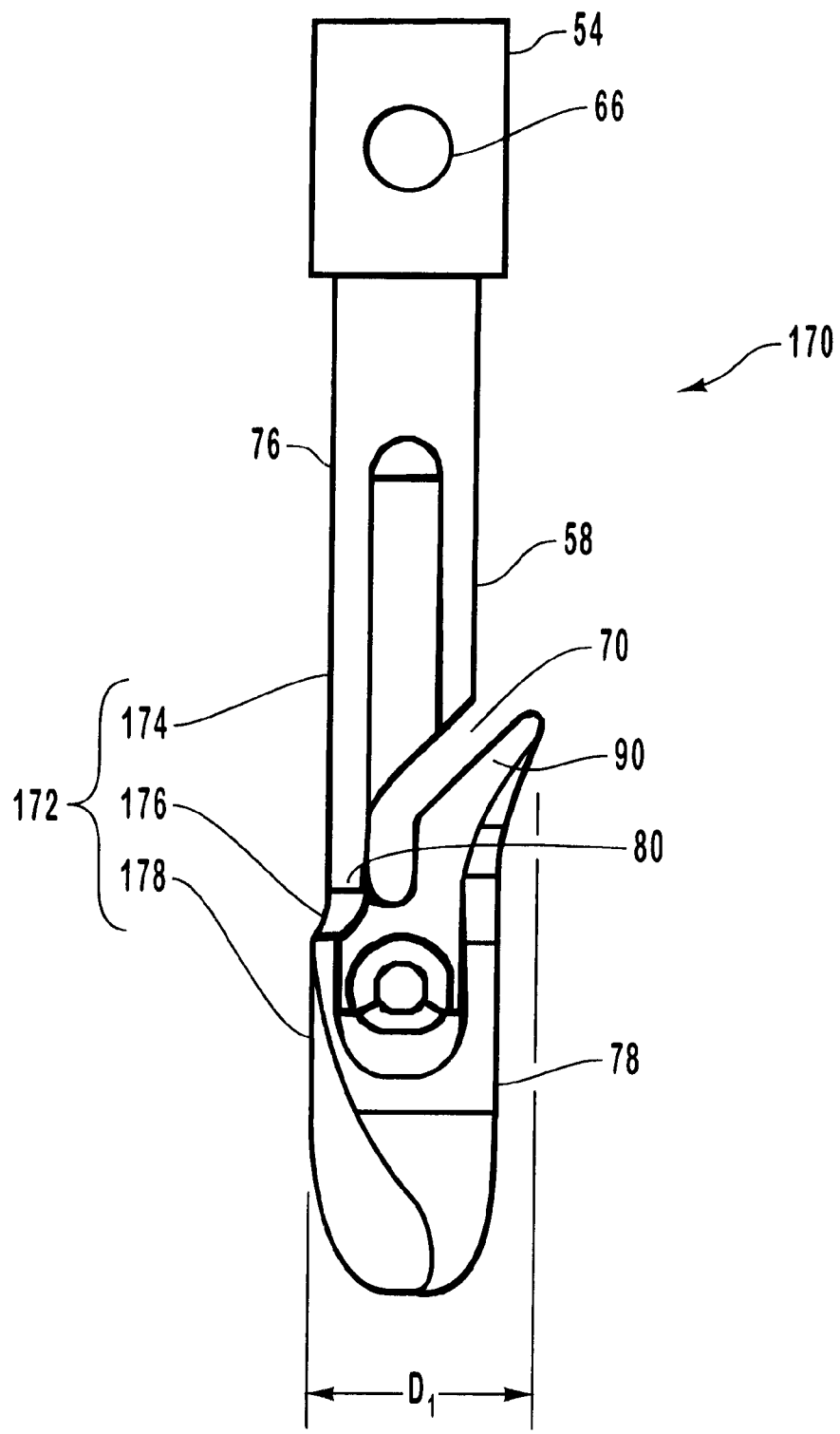
FIG. 18 is an elevated side view of another alternative embodiment of a suture anchor.

Depicted in FIG. 18 is another alternative embodiment of a suture anchor 170. Like elements between suture anchor 170 and suture anchor 12 are identified by like reference characters. Suture anchor 170 is distinguished from suture anchor 12 in that it comprises a back face 172 that includes a substantially linear first portion 174 that extends along placement portion 76, an outwardly sloping transition shoulder 176, and a second portion 178. Transition shoulder 176 generally begins to outwardly slope from first portion 174 at or just below the intended failure location of frangible strut 80. Alternatively, frangible strut 80 can also be designed to fail at a point along transition shoulder 176. Suture anchor 170 has a maximum diameter $D_1$ that transversely extends between back face 172 of attachment portion 78 and the tip of barb 90.

Figure 19:
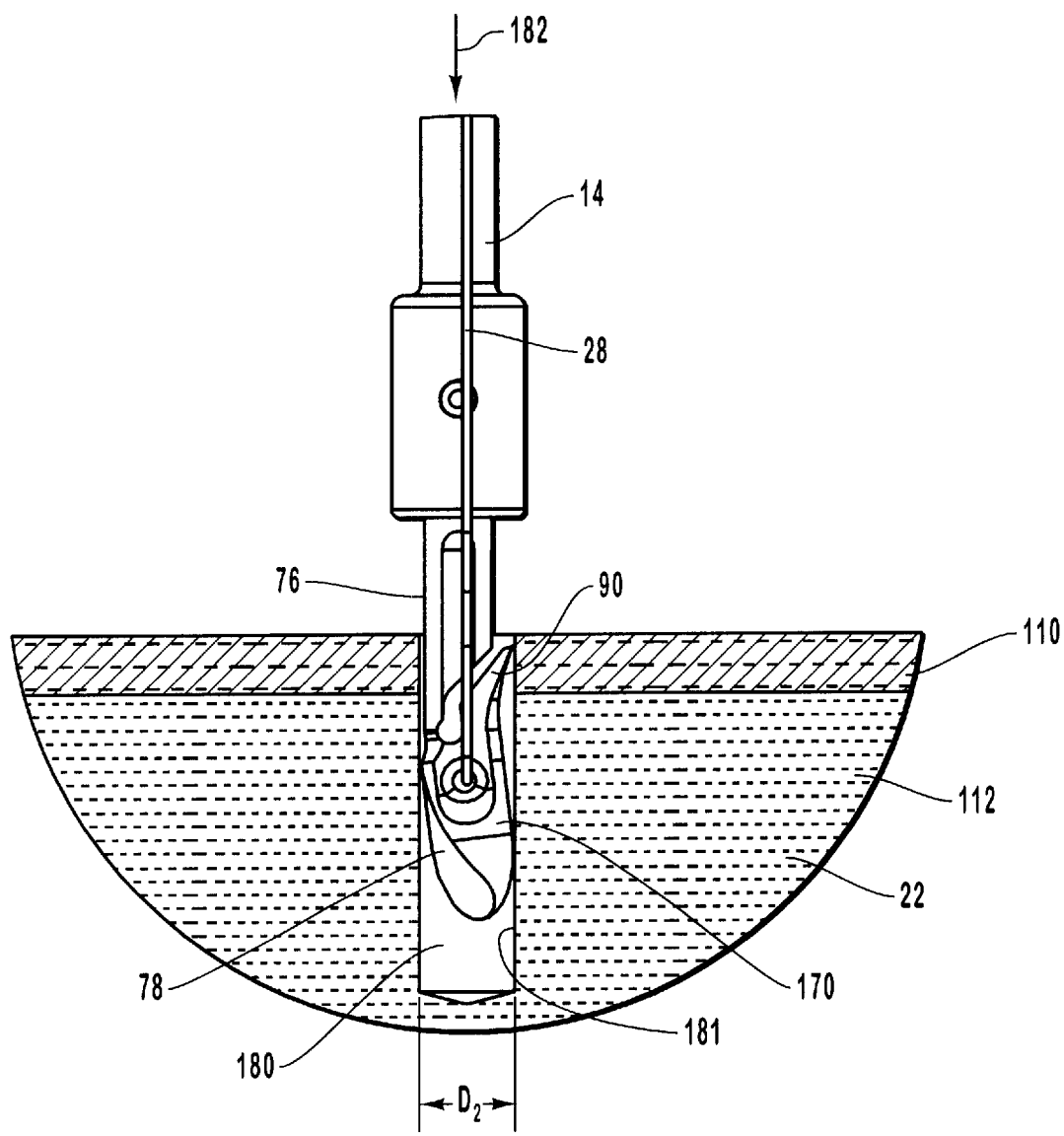
FIG. 19 is an elevated side view of the suture anchor shown in FIG. 18 being inserted into a single diameter bore hole.

Suture anchor 170 is placed by initially forming a single diameter bore hole 180 in bone 22, as depicted in FIG. 19. Bore hole 180 is bounded by an annular side wall 181 having a substantially constant diameter $D_2$. Diameter $D_2$ of bore hole 180 is smaller than diameter $D_1$ of suture anchor 170. Bore hole 180 can be formed using any conventional method.

Next, suture anchor 170 is inserted into bore hole 180 by applying a force in the direction of arrow 182 on inserter 14. As suture anchor 170 is advanced within bore hole 180, barb 90 contacts side wall 181 thereof. As additional force is applied, barb 90 causes attachment portion 78 to rotate slightly counter-clockwise (based on the view in FIG. 19) by either resiliently flexing under elastic deformation or bending under plastic deformation at frangible strut 80. In one embodiment using this configuration, depending on the hardness of the bone and the compositional material of suture anchor 170, all or substantially all of attachment portion 78, including barb 90, is received within bore hole 180 so that minimal or no scoring of bone 22 is produced but that attachment portion 78 is held within bore hole 180 by frictional engagement. In an alternative embodiment, attachment portion 78 can resiliently rotate in a clockwise direction once barb 90 passes cortical bone layer 110 so that barb 90 scores cancellous bone layer 112 as it is received therein.

Figure 20:
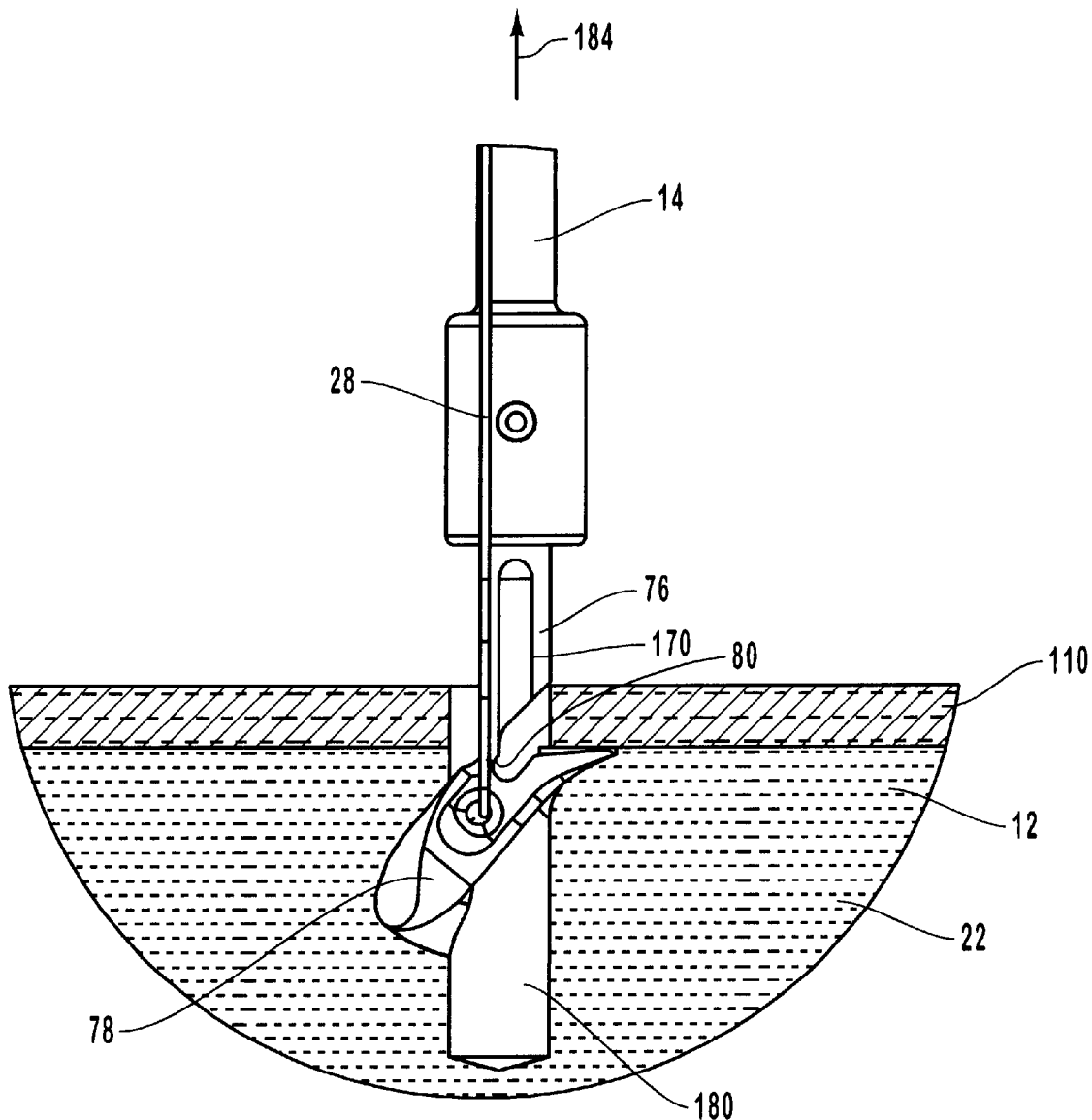
FIG. 20 is an elevated side view of the suture anchor shown in FIG. 19 being rotated within the bore hole.

As depicted in FIG. 20, once attachment portion 78 of suture anchor 170 is fully received within bore hole 180 to a desired depth, a withdrawal force, depicted by arrow 184, is applied to inserter 14. As a result, attachment portion 78 rotates clockwise within bore hole 180 (based on the view in FIG. 20) so that attachment portion 78 lodges by penetrating into bone 22. Attachment portion 78 continues to rotate until the failure of frangible strut 80. Suture line 28 can then be used to secure soft tissue in the same manner as previously discussed with regard to FIG. 15.

Figure 21A:
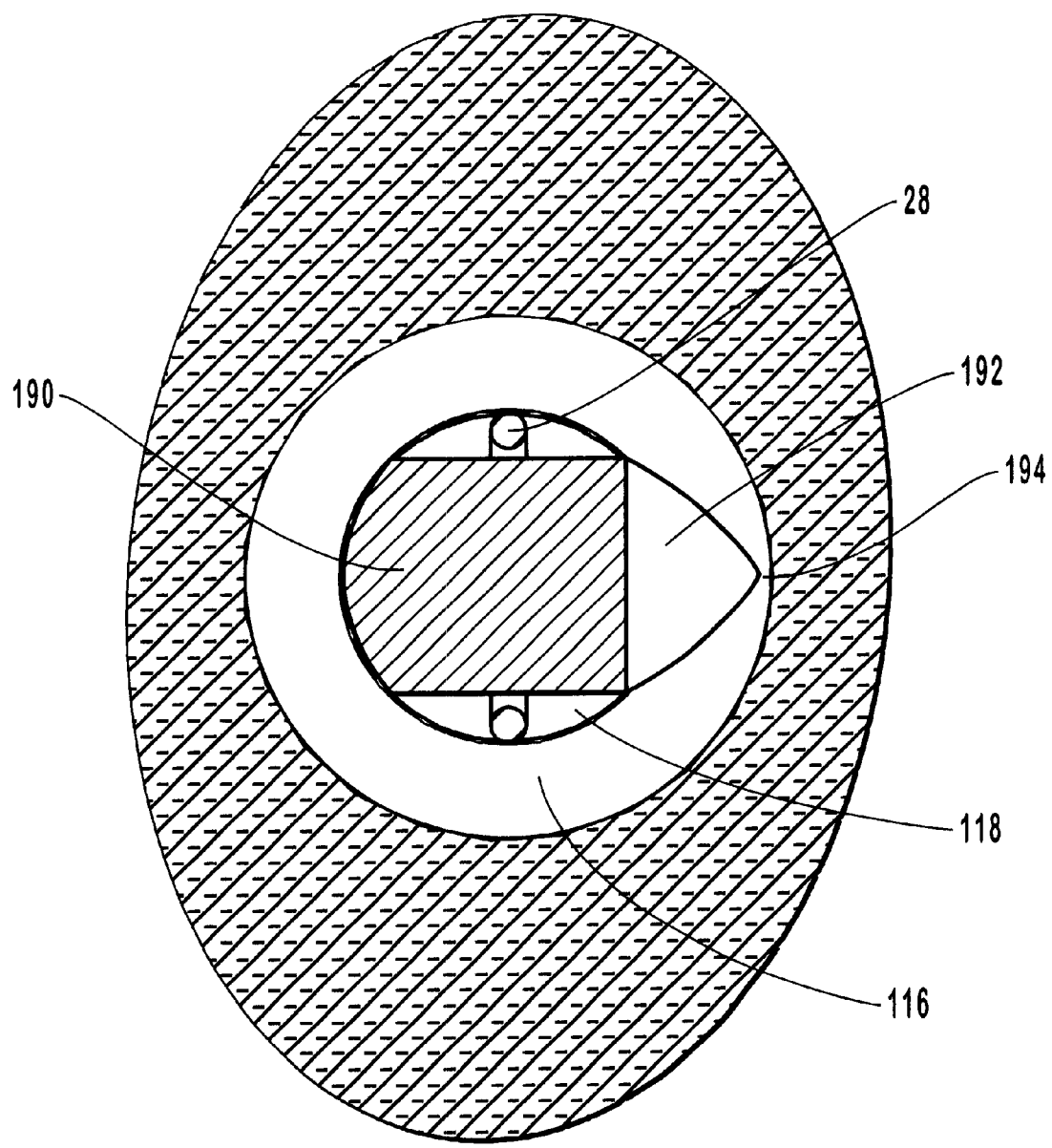
FIG. 21A is a cross sectional top plan view of an alternative embodiment of a suture anchor inserted within a bore hole, the suture anchor having a pointed barb.

It is appreciated that each of the various suture anchor embodiments discussed above can also have a variety of different transverse cross sectional configurations. By way of example and not by limitation, as depicted in FIG. 21A, which is a view comparable to FIG. 11, a suture anchor 190 is shown having a barb 192 that angles to a terminal point 194. Barb 192 is in contrast to barb 90 shown in FIG. 4 wherein barb 90 terminates at a linear edge 94.

Figure 21B:
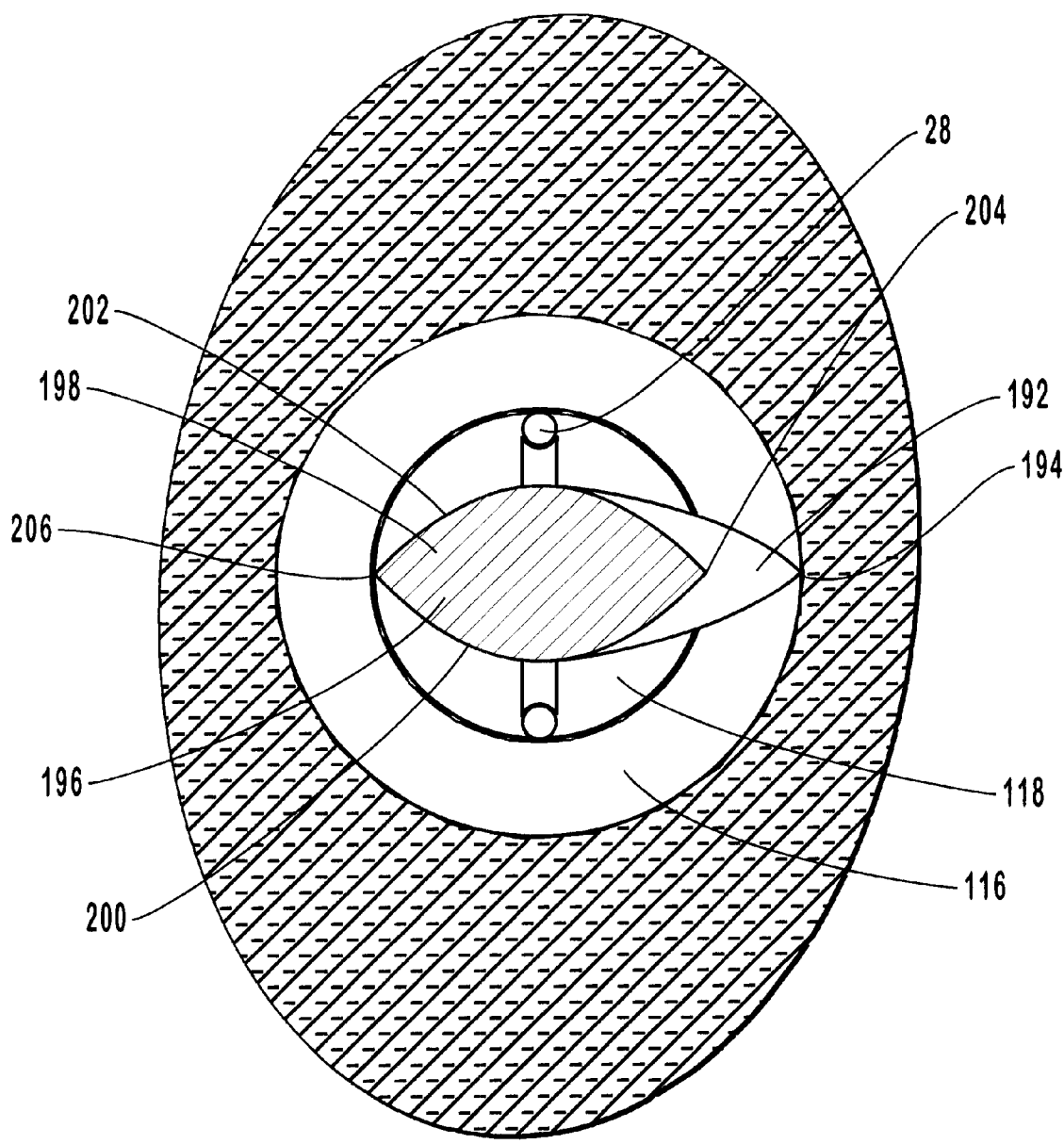
FIG. 21B is a cross sectional top plan view of an alternative embodiment of a suture anchor inserted within a bore hole, the suture anchor having a substantially eye-shaped transverse cross section.

In another embodiment, depicted in FIG. 21B, a suture anchor 196 is shown having a body 198 having a transverse cross sectional area that is substantially eye shaped. In this embodiment, body has opposing curved side walls 200 and 202 that extend between a front edge 204 and a back edge 206. The edges 204 and 206 assist in cutting into bone 22 when the corresponding attachment portion is rotated. Suture anchor 196 is shown having barb 192 that terminates at point 194, as discussed with FIG. 21A, but could also have barb 90 as discussed with suture anchor 12.

The various suture anchors of the present invention can be made in a variety of different ways using a variety of one or more different materials. By way of example and not by limitation, the various suture anchors can be made from medical grade bioabsorbable or non-absorbable materials. Examples of bioabsorbable materials include homopolymers and copolymers of lactide, glycolide, trimethylene carbonate, caprolactone, and p-dioxanone and blends or other combinations thereof and equivalents thereof. Examples of non-absorbable materials include metals such as stainless steel, titanium, Nitinol, cobalt, alloys thereof, and equivalents thereof and polymeric materials such as non-absorbable polyesters, polyamides, polyolefins, polyurethanes, and polyacetals and equivalents thereof.

In one embodiment, inserter 14 is made from the same material as the suture anchor or is made from a different material but one that is still a medical grade material, such as those discussed above. Alternatively, since inserter 14 is typically not inserted into the body of a patient, to minimize the cost of the suture anchor assembly, inserter 14 can also be made from a less expensive non-medical grade material. The material can be a metal, plastic, composite or the like. By making inserter 14 out of a less expensive material, it becomes economical to simply dispose of inserter 14 and the placement portion which is secured thereto once the attachment portion is separated. Inserter 14 and the suture anchor are disclosed as separate elements that are coupled together so that if desired, they can be made from different materials. Alternatively, inserter 14 and the suture anchor can be integrally formed as a single unit from the same material.

Figure 22:
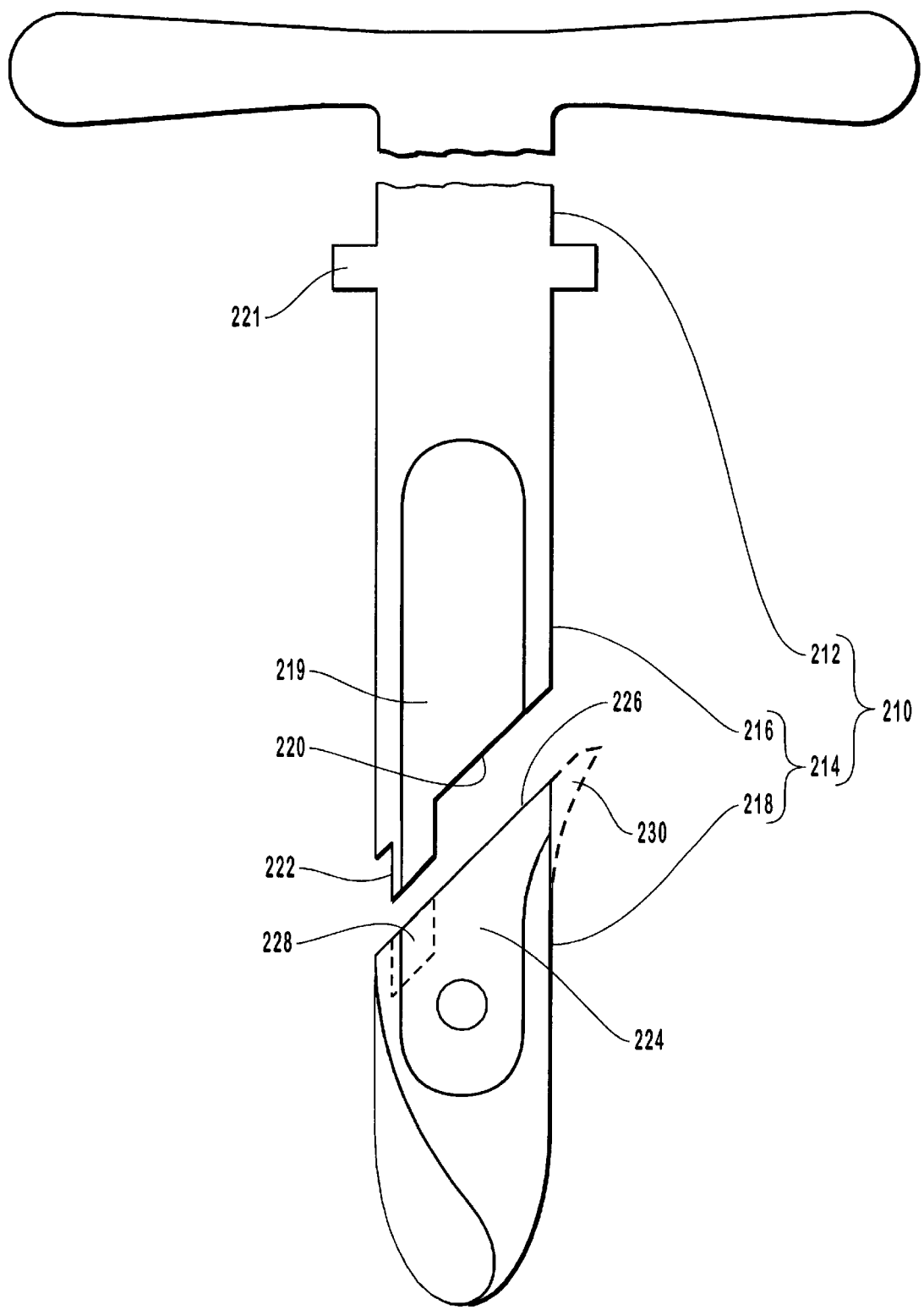
FIG. 22 is an elevated side view of a suture anchor assembly wherein the placement portion and the attachment portion thereof are selectively connected together.

Furthermore, in one embodiment each of the suture anchors discussed above, which each comprise a placement portion, attachment portion and frangible strut, are integrally formed as a single member. As used in the specification and appended claims, the term "integrally" is intended to mean that the associated element comprises a single continuous member as opposed to two or more members that are somehow connected together. In contrast to being integrally formed, however, the various suture anchors of the present invention can also be formed of separate elements that are connected together. For example, depicted in FIG. 22 is a suture anchor assembly 210 that includes an inserter 212 and a suture anchor 214. Suture anchor 214 includes a placement portion 216 and an attachment portion 218. Inserter 212 and placement portion 216 are integrally formed as a single unit. A flange stop 221 radially outwardly projects at the intersection of inserter 212 and placement portion 216. Placement portion 216 and attachment portion 218, however, are separate elements that are connected together.

More specifically, placement portion 216 has a distal end 219 that terminates at a distal end face 220. Downwardly projecting from distal end face 220 is a frangible strut 222. Attachment portion 218 has a proximal end 224 that terminates at a proximal end face 226. Formed on proximal end face 226 is a socket 228. Socket 228 is configured to receive at least a portion of frangible strut 222 therein. In this position, distal end face 220 and proximal end face 226 can be biased together or a space can be formed therebetween. Frangible strut 222 is secured within socket 228 such as by a press fitting, welding, adhesive, crimping or the like. Furthermore, the positioning of frangible strut 222 and socket 228 can be reversed. Furthermore, frangible strut 222 can be independently connected to both placement portion 216 and attachment portion 218.

Placement portion 216 is secured to attachment portion 218 such that attachment portion 218 can be secured within a bore hole such as by using one of the methods described herein. In this regard, attachment portion 218 can be formed with a barb 230, as depicted by the dashed lines, or without. Where attachment portion 218 is formed without barb 230, the bore hole is sized to sufficiently tightly receive attachment portion 218 on insertion so that attachment portion 218 rotates within the bore hole upon application of the extraction force as opposed to simply pulling out of the bore hole.

Each of the elements of the various suture anchor assemblies can be made from injection molding or other forms of molding. Furthermore, each of the various elements can be made by cutting or otherwise shaping extruded or other formed members.

Figure 23:
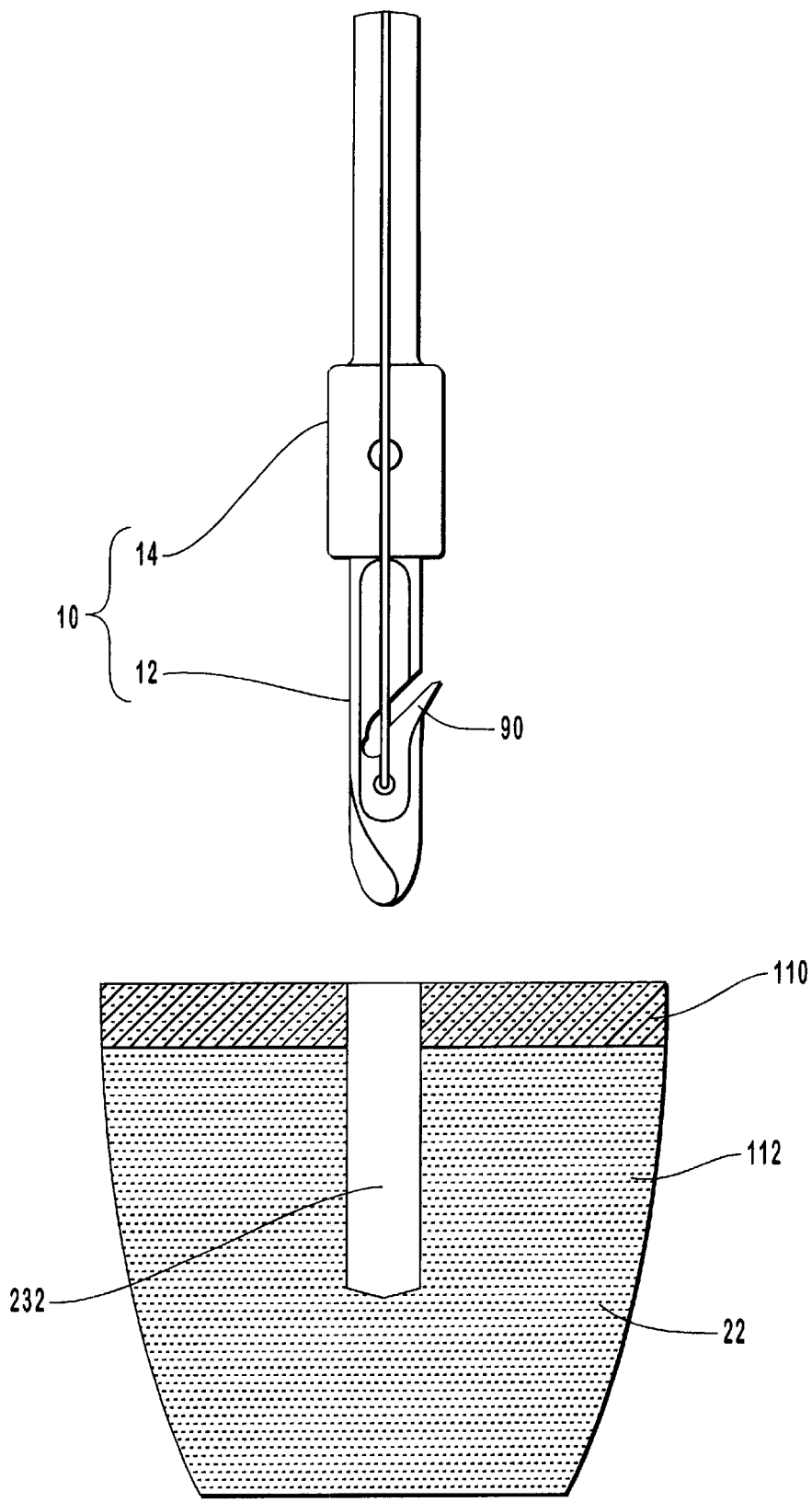
FIG. 23 is an elevated side view of a suture anchor designed for insertion within a single diameter bore hole.

It is also appreciated that the method of placement can also vary based on the type of material from which the suture anchor is made and the type of bone in which the suture anchor is placed. For example, depicted in FIG. 23 is suture anchor 12, as previously discussed, designed for insertion into a single diameter bore hole 232. Bore hole 232 has a diameter smaller than the transverse diameter of suture anchor 12 at the tip of barb 90. Accordingly, in one embodiment, to enable barb 90 to score cortical bone layer 110 and pass into cancellous bone layer 112, suture anchor 12 is comprised of a vary hard material such as, by way of example, titanium or stainless steel. In situations where bone 22 is softer, softer materials can be used for the same type of placement. Furthermore, where the bone is sufficiently soft, suture anchor 12 or other embodiments thereof, can be directly driven into bone 22 without the formation of a bore hole or with only a very small bore hole.

Figure 24:
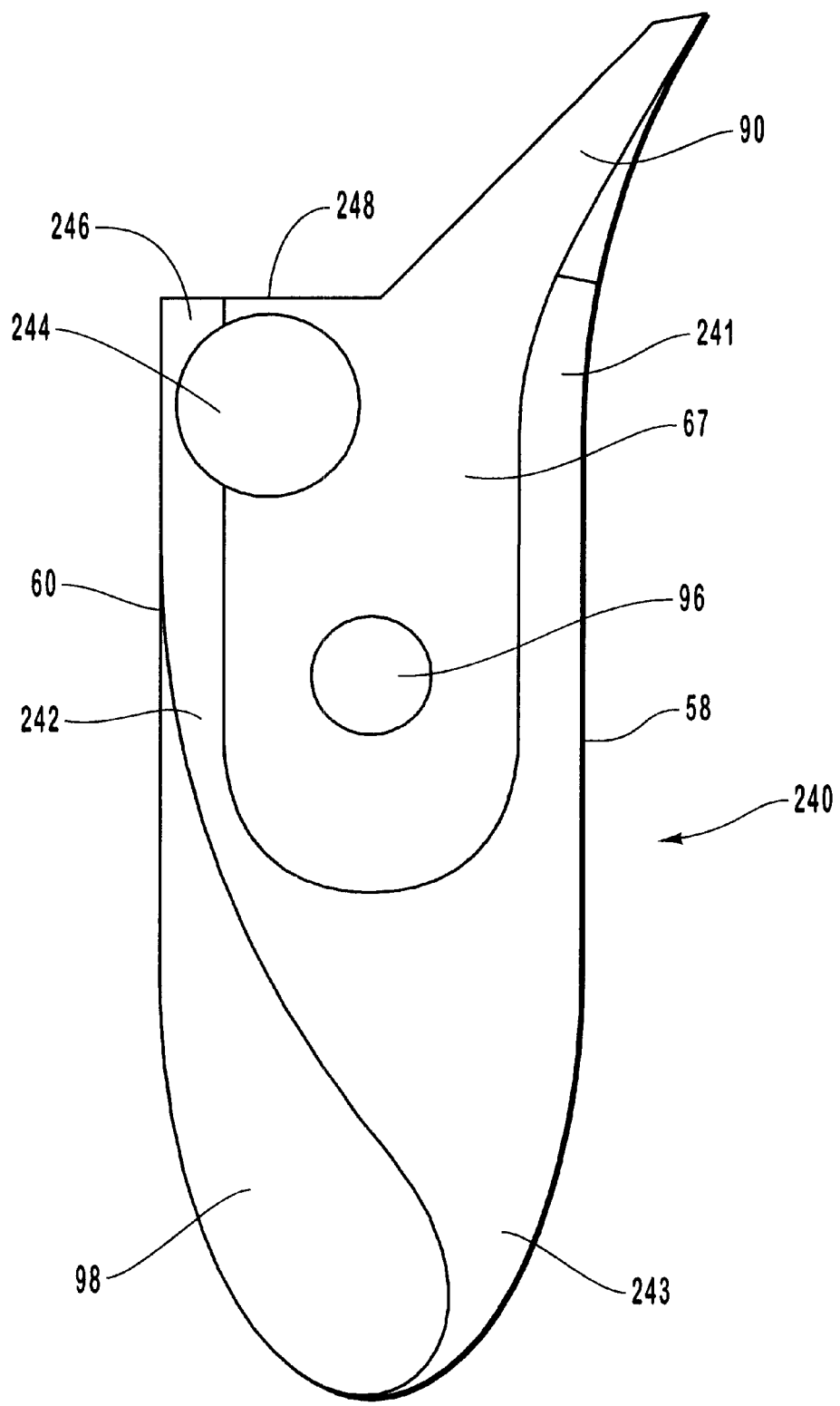
FIG. 24 is an elevated side view of another alternative embodiment of a suture anchor.

Depicted in FIG. 24 is another embodiment of a suture anchor 240. Suture anchor 240 has a configuration similar to attachment portion 78 of suture anchor 12 and as such like elements are identified by like reference characters. For example, suture anchor 240 has a body 242 that extends between a proximal end 241 and an opposing distal end 243. Proximal end 241 terminates at a proximal end face 248. Upwardly and outwardly projecting from proximal end face 248 is barb 90. Plow 98 is formed on back face 60 at distal end 243.

In contrast to attachment portion 78, however, suture anchor 240 has a mounting port 244 transversely extending between opposing flattened side walls 67 and 68 at proximal end 241. In the embodiment depicted, mounting port 244 has a substantially circular configuration. In alternative embodiments, mounting port 244 can have other polygonal or irregular configurations. Mounting port 244 is formed sufficiently close to back face 60 and/or proximal end face 248 that a frangible support 246 is formed between mounting port 244 and back face 60 and/or proximal end face 248.

Figure 25:
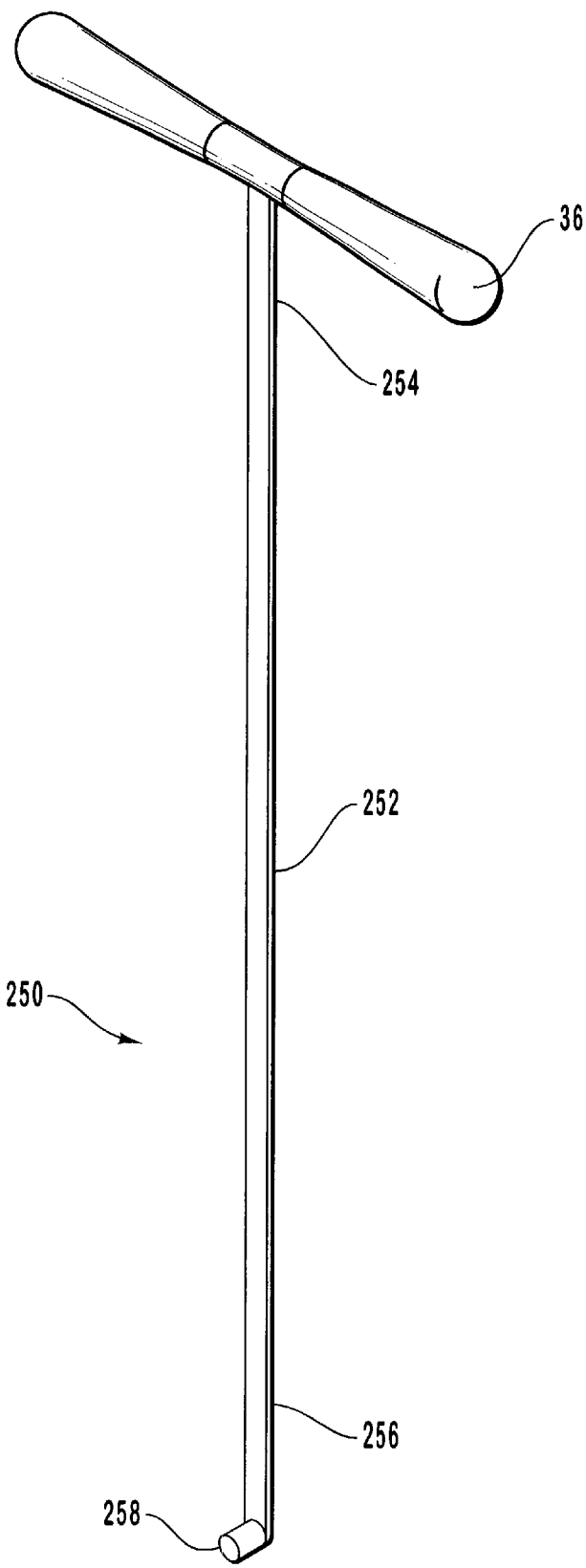
FIG. 25 is a perspective side view of an inserter used for the suture anchor shown in FIG. 24.

Depicted in FIG. 25 is an inserter 250. Inserter 250 comprises a thin elongated shaft 252 having a proximal end 254 and an opposing distal end 256. Formed at proximal end 254 is handle 36. Orthogonally projecting from distal end 256 is a cylindrical post 258.

Figure 26:
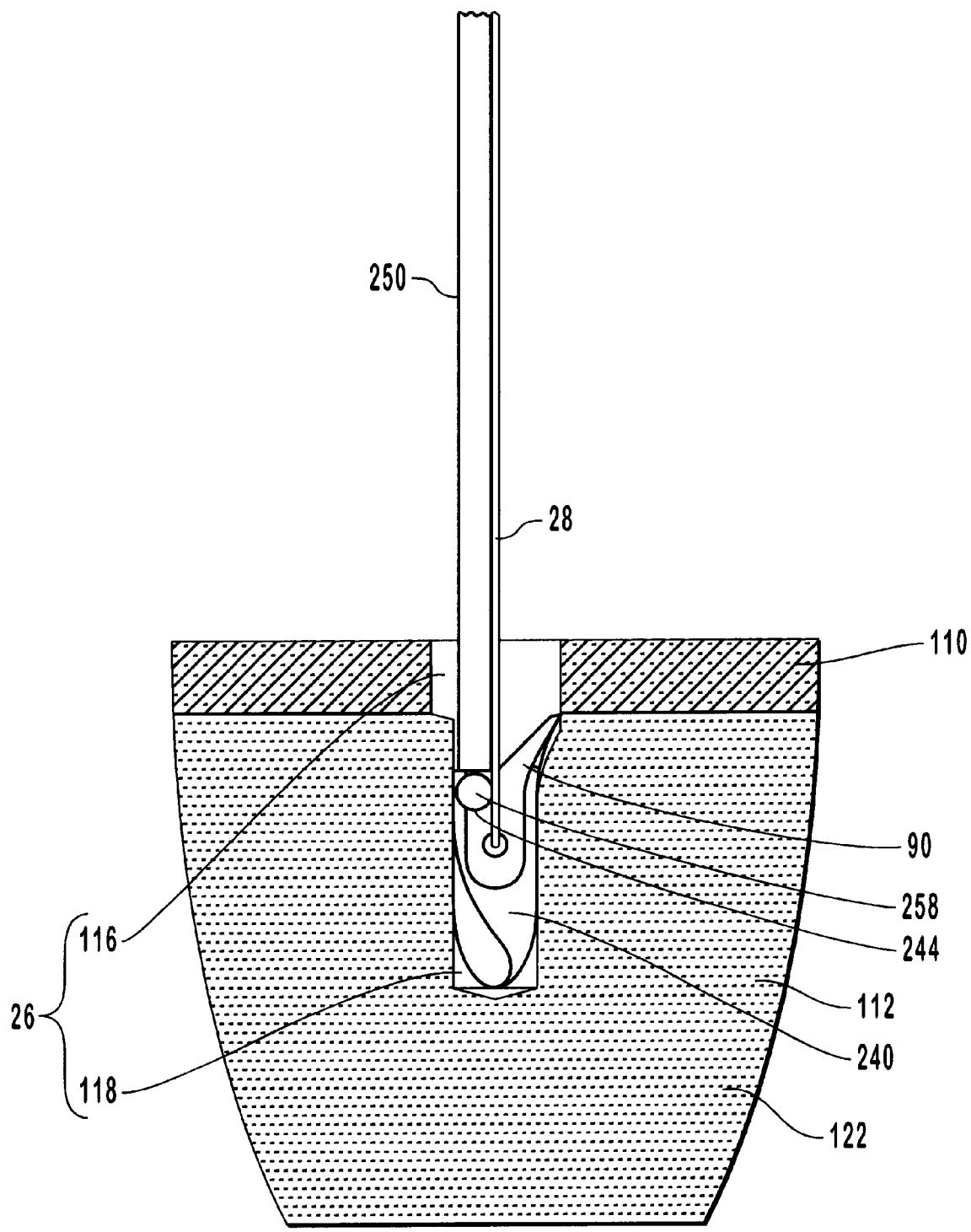
FIG. 26 is an elevated side view of the suture anchor shown in FIG. 24 being inserted with a bore hole by use of the inserter shown in FIG. 25.

During insertion, as depicted in FIG. 26, post 258 of inserter 250 is initially received within mounting port 244. Inserter 250 is then used to drive suture anchor 240 into bore hole 26 so that barb 90 scores cancellous bone layer 112 as it is received therein.

Figure 27:
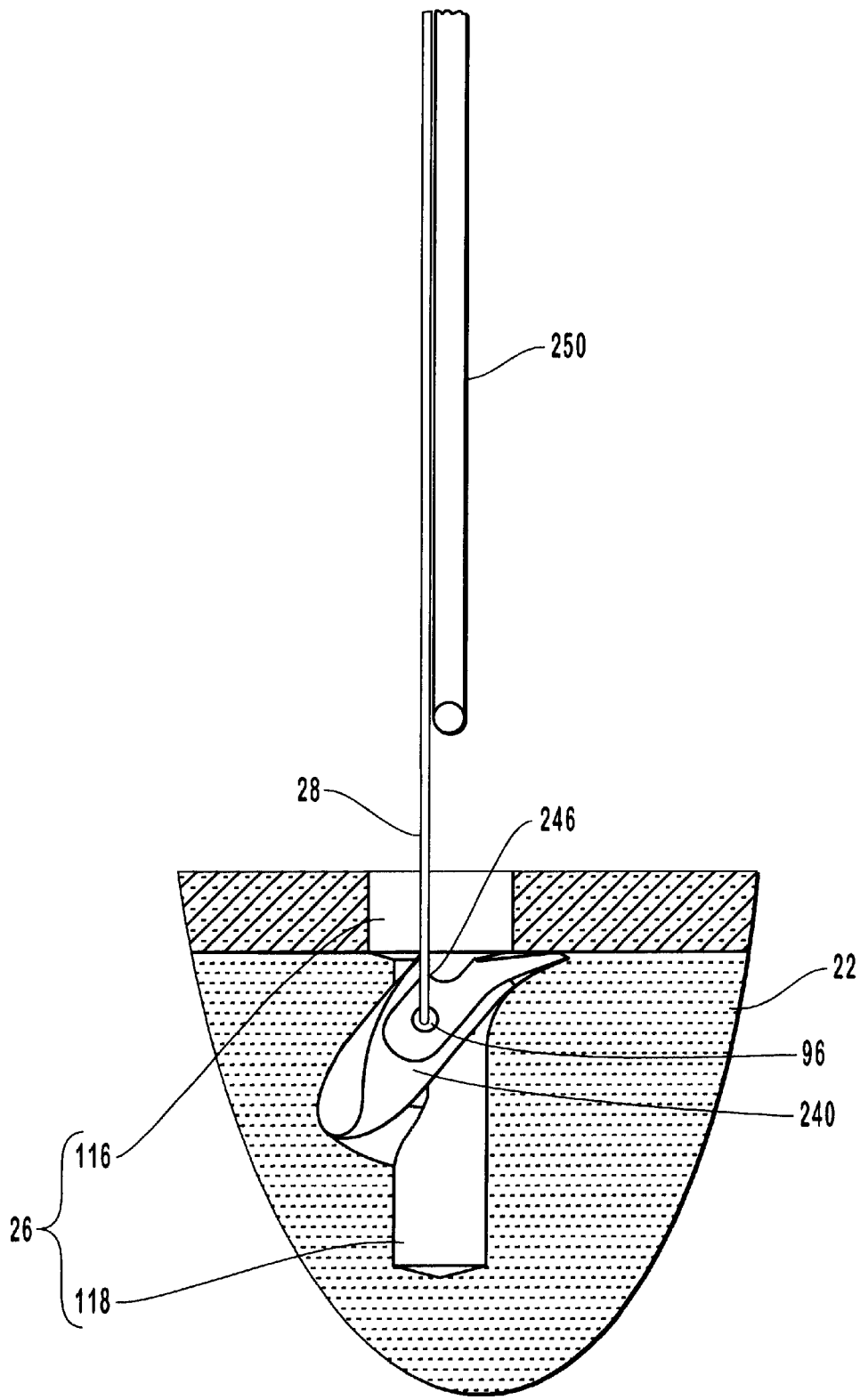
FIG. 27 is an elevated side view of the suture anchor shown in FIG. 26 being rotated within the bore hole.

Once suture anchor 240 is inserted, a withdrawal force is applied to inserter 250 causing suture anchor 240 to rotate within bore hole 26 about post 258. Suture anchor 240 continues to rotate until a sufficient force is applied by post 258 of inserter 250 on frangible support 246 to produce failure of frangible support 246, as shown in FIG. 27. Once frangible support 246 fails, inserter 250 is removed from bore hole 26 and suture line 28 is used to secure the soft tissue.

The present invention may be embodied in other specific forms without departing from its spirit or essential characteristics. For example, it is appreciated that the various elements and features of above described suture anchor assemblies can be exchanged between the different embodiments. Furthermore, expressed alternatives or modifications to one embodiment are also applicable to the other embodiments. The described embodiments are thus to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for securing a suture anchor, the method comprising:
    inserting an attachment portion of a suture anchor within a bore hole formed in a bone, the suture anchor further comprising a placement portion frangably connected to the attachment portion, the attachment portion of the suture anchor having an outwardly projecting barb that scores at least a portion of the bone bounding the bore hole as the attachment portion is inserted into the bore hole;
    applying a withdrawal force to the suture anchor such that the attachment portion of the suture anchor rotates within the bore hole and disconnects from the placement portion of the suture anchor; and
    removing the placement portion from the bone such that the attachment portion remains within the bone.

2. A method as recited in claim 1, wherein outwardly projecting barb scores the bone by a depth of at least 0.5 mm.

3. A method as recited in claim 1, wherein the bore hole comprises a first hole having a maximum first diameter and a concentrically disposed second hole having a maximum second diameter, the first hole being formed on a top surface of the bone while the second hole is formed below the top surface of the bone, the maximum second diameter being smaller than the maximum first diameter, the act of inserting comprising the attachment portion being inserted within the second hole.

4. A method as recited in claim 1, wherein the placement portion has a distal end face and the attachment portion has a proximal end face, the distal end face facing the proximal end face and being spaced apart therefrom, the act of inserting comprising inserting the attachment portion within the bore hole such that the attachment portion or the placement portion moves so that at least a portion of the proximal end face biases against at least a portion of the distal end face.

5. A method as recited in claim 1, wherein the attachment portion and the placement portion comprise an integral element comprised of a first material, an elongated inserter comprised of a second material different than the first material being attached to the placement portion, the act of inserting comprising applying a force to the inserter so as to insert the attachment portion into the bore hole, the act of removing the placement portion comprising applying a further withdrawal force to the inserter such that the placement portion is withdrawn from the bone while remaining attached to the inserter.

6. A method as recited in claim 1, wherein the act of applying a withdrawal force comprises applying a withdrawal force to the placement portion of the suture anchor such that the placement portion causes the attachment portion of the suture anchor to rotate within the bore hole and disconnect from the placement portion of the suture anchor.

7. A method as recited in claim 1, wherein the bore hole has a transverse cross sectional area with a first diameter and the suture anchor has a transverse cross sectional area at the barb with a maximum second diameter, the act of inserting the attachment portion of the suture anchor within the bore hole comprising the second diameter being larger than the first diameter such that the barb scores the portion of the bone bounding the bore hole as the attachment portion is inserted into the bore hole.

8. A method for securing a suture anchor, the method comprising:
    forming a bore hole within a bone, the bore hole comprising a first hole having a maximum first diameter and a concentrically disposed second hole having a maximum second diameter, the first hole being formed on a top surface of the bone while the second hole is formed below the top surface of the bone, the maximum second diameter being smaller than the maximum first diameter;
    inserting an attachment portion of a suture anchor within the second hole of the bore hole such that at least a portion of the attachment portion of the suture anchor biases in frictional engagement against at least a portion of the bone bounding the second hole, the suture anchor further comprising a placement portion frangably connected to the attachment portion; and
    applying a withdrawal force to the suture anchor such that the attachment portion of the suture anchor rotates within the bore hole and disconnects from the placement portion of the suture anchor.

9. A method as recited in claim 8, wherein the attachment portion of the suture anchor has an outwardly projecting barb that scores at least a portion of the bone bounding the second hole of the bore hole as the attachment portion is inserted into the bore hole.

10. A method as recited in claim 8, wherein the bore hole is formed by a drill bit.

11. A method as recited in claim 8, wherein the bore hole is formed by a punch.

12. A method as recited in claim 8, wherein the placement portion has a distal end face and the attachment portion has a proximal end face, the distal end face facing the proximal end face and being spaced apart therefrom, the act of inserting comprising inserting the attachment portion within the bore hole such that the attachment portion or the placement portion moves so that at least a portion of the proximal end face biases against at least a portion of the distal end face.

13. A method as recited in claim 8, wherein the attachment portion and the placement portion comprise an integral element comprised of a first material, an elongated inserter comprised of a second material different than the first material being attached to the placement portion, the act of inserting comprising applying a force to the inserter so as to insert the attachment portion into the bore hole.

14. A method for securing a suture anchor, the method comprising:
inserting at least a portion of a suture anchor within a bore hole formed on a bone, the suture anchor comprising a placement portion terminating at a distal end face and an attachment portion having a proximal end face, the placement portion being frangibly connected to the attachment portion such that at least a portion of the distal end face of the placement portion is spaced apart from the proximal end face of the attachment portion, the attachment portion biasing in frictional engagement against at least a portion of the bone bounding the bore hole as the suture anchor is inserted into the bore hole such that at least the proximal end face of the attachment portion or the distal end face of the placement portion moves so that at least a portion of the distal end face and the proximal end face bias together during the act of inserting; and
applying a withdrawal force to the suture anchor such that the attachment portion of the suture anchor rotates within the bore hole causing the placement portion to disconnect from the attachment portion; and
removing the placement portion from the bone such that the attachment portion remains within the bone.

15. A method as recited in claim 14, wherein the attachment portion of the suture anchor has an outwardly projecting barb, the barb scoring at least a portion of the bone bounding the bore hole as the attachment portion is inserted into the bore hole.

16. A method as recited in claim 14, wherein the attachment portion and the placement portion comprise an integral element comprised of a first material, an elongated inserter comprised of a second material different than the first material being attached to the placement portion, the act of inserting comprising applying a force to the inserter so as to insert the attachment portion into the bore hole.

17. A method as recited in claim 14, wherein the bore hole comprises a first hole having a maximum first diameter and a concentrically disposed second hole having a maximum second diameter, the maximum second diameter being smaller than the maximum first diameter, the act of inserting comprising the attachment portion being inserted within the second hole.

18. A method as recited in claim 14, wherein a frangible strut extends between the placement portion and the attachment portion.

19. A suture anchor for use within a bore hole formed in a bone, the suture anchor comprising:
a placement portion;
an attachment portion comprising a body that terminates at a distal terminus, the body having a barb outwardly projecting therefrom at a distance proximal of the distal terminus, the barb being adapted to score at least a portion of the bone bounding the bore hole as the attachment portion is being inserted within the bore hole; and
means for connecting the placement portion to the attachment portion such that when an insertion force is applied to the placement portion and the attachment portion as they are being directed into the bore hole, the barb scores at least a portion of the bone bounding the bore hole while maintaining connection between the placement portion and the attachment portion and when a withdrawal force, substantially opposite of the insertion force, is applied to the placement portion and the attachment portion, the attachment portion rotates within the bore hole causing the placement portion and the attachment portion to disconnect.

20. A suture anchor as recited in claim 19, wherein the means for connecting comprises a frangible strut extending between the placement portion and the attachment portion.

21. A suture anchor as recited in claim 20, wherein the attachment portion, placement portion, and frangible strut are each comprised of a bioabsorbable material.

22. A suture anchor as recited in claim 20, wherein the frangible strut projects from one of the placement portion or the attachment portion and connects with the other thereof.

23. A suture anchor as recited in claim 20, wherein a slot bounded between attachment portion and the placement portion is formed adjacent to the frangible strut.

24. A suture anchor as recited in claim 20, wherein the attachment portion, placement portion, and frangible strut comprise a unitary integral member.

25. A suture anchor as recited in claim 19, wherein the body of the attachment portion has a front face and an opposing back face each extending between a proximal end and an opposing distal end, the barb outwardly projecting from the font face of the body away from the back face.

26. A suture anchor as recited in claim 25, further comprising a tapered plow formed on the back face of the attachment portion.

27. A suture anchor as recited in claim 19, further comprising a suture port extending through the attachment portion.

28. A suture anchor as recited in claim 19, further comprising means for coupling a suture line to the attachment portion.

29. A suture anchor as recited in claim 19, further comprising an elongated inserter attached to the placement portion.

30. A suture anchor as recited in claim 29, wherein the inserter is comprised of a material different than that of the placement portion.

31. A suture anchor as recited in claim 19, wherein the body of the attachment portion has a proximal end attached to the placement portion and an opposing free distal end, the barb projecting from the proximal end of the body.

32. A suture anchor for attachment to a bone, the suture anchor comprising:
an elongated body having a first face and an opposing second face each longitudinally extending between a proximal end and an opposing distal end, the body having a central longitudinal axis extending between the proximal end and the opposing distal end;
a slot starting at the first face and extending towards the second face so as to partially bisect the elongated body, the slot being bounded by an upper side wall and a lower side wall;
a frangible strut extending between the slot and the second face of the body, the frangible strut forming a portion of the body; and
a barb outwardly projecting from the first face or the second face of the body at a location distal of at least a portion of the slot, the body having a transverse cross section substantially normal to the longitudinal axis at the location of the barb with a maximum first diameter and a transverse cross section substantially normal to the longitudinal axis at a location distal of the barb with a maximum second diameter, the first diameter being greater than the second diameter.

33. A suture anchor as recited in claim 32, further comprising means for coupling a suture line to the body at a location distal of the slot.

34. A suture anchor as recited in claim 33, wherein the means for securing the suture line comprises a suture port transversely extending through the body at the location distal of the slot so that the suture port is at least substantially normal to the longitudinal axis.

35. A suture anchor as recited in claim 32, wherein the slot bounds at least a portion of a surface of the barb.

36. A suture anchor as recited in claim 32, further comprising a tapered plow formed on the second face of the body.

37. A suture anchor as recited in claim 32, further comprising an inserter securely coupled with the body, the inserter being comprised of a material different than the body.

38. A suture anchor as recited in claim 32, wherein the slot terminates at a rounded end face that at least partially bounds the frangible strut.

39. A suture anchor as recited in claim 32, wherein the body comprises a first side face at least substantially disposed in a first plane and a second side face at least substantially disposed in a second plane, the first plane and the second plane being disposed in parallel alignment.

40. A suture anchor as recited in claim 32, wherein the body has a longitudinal section having a transverse cross section normal to the longitudinal axis, the transverse cross section being substantially round with opposing side faces, the side faces being at least substantially straight or concaved.

41. A suture anchor assembly comprising:
   a suture anchor comprising:
      an elongated placement portion having a proximal end and an opposing distal end; and
      an elongated attachment portion having a proximal end, an opposing distal end and an outwardly projecting barb, the distal end of the placement portion being frangibly connected to the proximal end of the attachment portion, the placement portion and the attachment portion being integrally formed together as a single member which is comprised of a first material; and
   an elongated inserter coupled to the proximal end of the placement portion, the inserter being comprised of a second material, the second material being different from the first material.

42. A suture anchor assembly as recited in claim 41, further comprising a frangible strut extending between the attachment portion and the placement portion, the strut being integrally formed with the attachment portion and the placement portion.

43. A suture anchor assembly as recited in claim 41, further comprising means for coupling a suture line to the attachment portion.

44. A suture anchor assembly as recited in claim 41, wherein the inserter is coupled in a fixed engagement with the placement portion.

45. A suture anchor assembly comprising:
   an elongated inserter having a post outwardly projecting from an end thereof; and
   a suture anchor comprising a body having a barb outwardly projecting therefrom, the body comprising a first side and an opposing second side each extending between a proximal end and an opposing distal end, the body bounding a mounting port extending from the first side to or toward the second side, the post of the inserter being rotatably disposed within the mounting port, at least a portion of the body bounding the mounting port being selectively frangible to enable separation of the inserter and the suture anchor.

46. A suture anchor assembly as recited in claim 45, further comprising means for coupling a suture line to the suture anchor.

47. A suture anchor assembly as recited in claim 45, wherein the barb is adapted to score bone upon insertion of the suture anchor within a bore hole formed in the bone.

48. A suture anchor assembly as recited in claim 45, wherein the means for coupling a suture line to the suture anchor comprises a suture port extending from the first side of the body to the opposing second side.

49. A suture anchor assembly as recited in claim 45, wherein the inserter comprises an elongated shaft having the post projecting substantially orthogonally from an end thereof.

* * * * *

UNITED STATES PATENT AND TRADEMARK OFFICE
CERTIFICATE OF CORRECTION

PATENT NO. : 6,645,227 B2
DATED : November 11, 2003
INVENTOR(S) : Fallin et al.

It is certified that error appears in the above-identified patent and that said Letters Patent is hereby corrected as shown below:

Column 2,
Line 60, replace "Sutures" with -- Suture --

Column 5,
Line 33, replace "extended" with -- extend --

Column 7,
Line 22, replace "embodiment" with -- embodiments --
Line 58, after "way" insert -- as --

Column 8,
Line 10, after "oriented" replace "a" with -- at --
Line 11, replace "angle" with -- angle. --

Column 9,
Line 12, after "body" insert -- 198 --

Column 10,
Line 41, before "hard" replace "vary" with -- very --

Column 13,
Line 25, after "inserting;" remove "and"

Column 14,
Line 29, replace "font" with -- front --

Signed and Sealed this

Thirteenth Day of July, 2004

JON W. DUDAS
*Acting Director of the United States Patent and Trademark Office*